(12) United States Patent
Lu et al.

(10) Patent No.: US 6,495,376 B1
(45) Date of Patent: Dec. 17, 2002

(54) METHODS AND COMPOSITIONS FOR REGULATING PROTEIN-PROTEIN INTERACTIONS

(75) Inventors: Kun Ping Lu, Newton, MA (US); Xiao Zhen Zhou, Newton, MA (US)

(73) Assignee: Beth Israel Deaconess Medical Center, Boston, MA (US)

( * ) Notice: Subject to any disclaimer, the term of this patent is extended or adjusted under 35 U.S.C. 154(b) by 0 days.

(21) Appl. No.: 09/252,404

(22) Filed: Feb. 18, 1999

(51) Int. Cl.[7] ............................................. G01N 33/566
(52) U.S. Cl. ........................... 436/501; 435/4; 435/7.1; 435/7.6; 435/7.72; 435/7.93; 435/7.94; 435/7.95; 530/300; 530/350
(58) Field of Search ..................... 435/4, 7.93, 7.94, 435/7.95, 7.1, 7.92, 7.72, 7.6; 436/501; 530/300, 323, 350, 388.1, 389.1

(56) References Cited

U.S. PATENT DOCUMENTS

| | | | |
|---|---|---|---|
| 4,584,377 A | 4/1986 | Yokoi et al. | 546/15 |
| 4,612,132 A | 9/1986 | Wollenberg et al. | 252/51.5 |
| 4,673,678 A | 6/1987 | Misra | 514/278 |
| 5,166,208 A | 11/1992 | Kelly et al. | 514/278 |
| 5,532,167 A | 7/1996 | Cantley et al. | 436/89 |
| 5,643,873 A | 7/1997 | Barrett et al. | 514/12 |
| 5,654,276 A | 8/1997 | Barrett et al. | 514/13 |
| 6,011,137 A | 1/2000 | Pirozzi et al. | 530/324 |

FOREIGN PATENT DOCUMENTS

| | | |
|---|---|---|
| FR | 2740454 | 4/1997 |
| WO | WO 97/12962 | 4/1997 |
| WO | WO 97/17986 | 5/1997 |
| WO | WO 97/37223 | 10/1997 |
| WO | WO 99/12962 | 3/1999 |

OTHER PUBLICATIONS

Abaza et al. Effects of amino acid substitutions outside an antigenic site on protein binding to . . . Journal of Protein Chemistry (1992) vol. 11, No. 5, pp. 433–444.*
Lazar et al. Transforming growth factor alpha: mutation of Asp 47 and Leu 48 results in different biological activities. Molecular and Cellular Biology (1988) vol. 8, No. 3, pp. 1247–1252.*
Lu, P.–J. et al., "Function of WW domains as phosphoserine or phosphothreonine– binding modules," *Science*, 283(5406):1325–1328 (1999).
Lu, P.–J. et al., "A novel function of WW domains as regulated phosphoserine–binding modules," *FASEB J.*, 13(7):A1510 (1999).
Lu, P.–J. et al., "The prolyl isomerase pin 1 restores the function of Alzheimer–associated phosphorylated tau protein," *Nature (London)*, 399(6738):784–788 (1999).
Michalak Marek et al. "Phosphorylation of the carboxyl–terminal region of dystrophin," *Biochemistry and Cell Biology*, 74(4):431–437 (1996).

Sabo, S. et al. "Regulation of beta–amyloid secretion by FE65, an amyloid protein precursor–binding protein," *J. Biological Chemistry*, 274(12):7952–7957 (1999).
Spillantini, M.G. et al. "Tau protein pathology in neurodegenerative diseases," *Trends in Neurosciences*, 21(10):428–432 (1998).
Zhou, X.Z. et al., "Phosphorylation–dependent prolyl isomerization: a novel signaling regulatory mechanism," *Cellular and Molecular Life Sciences*, 56:788–806 (1999).
Lu, K.P., et al., "Evidence for a NIMA–Like Mitotic Pathway in Vertebrate Cells," *Cell*, 81:413–424 (1995).
Ranganathan, R., et al., "Structural and Functional Analysis of the Mitotic Rotamase Pin1 Suggests Substrate Recognition is Phosphorylation Dependent," *Cell*, 89:875–886 (1997).
Lu, K.P., et al., "A Human Peptidyl–Prolyl Isomerase Essential for Regulation of Mitosis," *Nature*, 380:544–547 (1996).
Saragovi, H.U., et al., "Loops and Secondary Structure Mimetics: Development and Applications in Basic Science and Rational Drug Design," *Bio/Technology*, 10:773–778 (1992).
Songyang, Z., et al., "SH2 Domains Recognize Specific Phosphopeptide Sequences," *Cell*, 72:767–778 (1993).
Burke Jr., T.R., et al., "Nonhydrolyzable Phosphotyrosyl Mimetics for the Preparation of Phosphatase–Resistant SH2 Domain Inhibitors," *Biochemistry*, 33:6490–6494 (1994).
Knappik, A. and Plückthun, A., "Engineered Turns of a Recombinant Antibody Improve its In Vivo Folding," *Protein Engineering*, 8:81–89 (1995).
Maraganore, J.M., "Design and Characterization of Hirulogs: A Novel Class of Bivalent Peptide Inhibitors of Thrombin," *Biochemistry*, 29:7095–7101 (1990).
Keane, A.M., et al., "Peptide Mimetics of an Actin–Binding Site on Myosin Span Two Functional Domains on Actin," *Nature*, 344:265–268 (1990).
Wells, J.A., "Hormone Mimicry," *Science*, 273:449–450 (1996).

(List continued on next page.)

*Primary Examiner*—Jeffrey Stucker
*Assistant Examiner*—Ulrike Winkler
(74) *Attorney, Agent, or Firm*—Lahive & Cockfield, LLP; Elizabeth A. Hanley, Esq.; Cynthia L. Kanik, Esq.

(57) ABSTRACT

The invention relates to methods and compositions of WW-domains as phosphoserine and phosphothreonine binding modules. The WW-domain containing polypeptides of the invention can be used, for example, to regulate cell growth; to treat neurodegenerative diseases; to screen for substances that modulated interactions between WW-domain containing polypeptides and phosphorylated ligands; as drug targeting vehicles; to direct protein degradation; and in the treatment of certain diseases or conditions characterized by aberrant WW-domain containing polypeptides or their ligands.

7 Claims, 6 Drawing Sheets

OTHER PUBLICATIONS

Livnah, O., et al., "Functional Mimicry of a Protein Hormone by a Peptide Agonist: The EPO Receptor Complex at 2.8 Å," *Science, 273*:464–471 (1996).

Wrighton, N.C., "Small Peptides as Potent Mimetics of the Protein Hormone Erythopoietin," *Science, 273*:458–463 (1996).

Saragovi, H.U., et al., "Design and Synthesis of a Mimetic From an Antibody Complementarity–Determining Region," *Science, 253*:792–795 (1991).

Baily, E,. et al., "Phosphorylation of Two Small GTP–Binding Proteins of the Rab Family by p34$^{cdc2}$," *Nature, 350*:715–718 (1991).

Lu, K.P., et al., "A Human Peptidyl–Prolyl Isomerase Essential for Regulation of Mitosis," *Nature, 380*:544–547 (1996).

Schreiber, S.L., "Chemistry and Biology of the Immunophilins and Their Immunosuppressive Ligands," *Science, 251*:283–287 (1991).

Kumagai, A. and Dunphy, W.G., "Purification and Molecular Cloning of Plx1, a Cdc25–Regulatory Kinase from Xenopus Egg Extracts," *Science, 273*:1377–1380 (1996).

Heald, R. and McKeon F., "Mutations of Phosphorylation Sites in Lamin A That Prevent Nuclear Lamina Disassembly in Mitosis," *Cell, 61*:579–589 (1990).

Blangy, A., et al., "Phosphorylation by p34$^{cdc2}$ Regulates Spindle Association of Human Eg5, a Kinesin–Related Motor Essential for Bipolar Spindle Formation In Vivo," *Cell, 83*:1159–1169 (1995).

Nurse, P., "Ordering S Phase and M Phase in the Cell Cycle," *Cell, 79*:547–550 (1994).

King, R.W., et al., "Mitosis in Transition," *Cell, 79*:563–571 (1994).

Solomon, M.J., et al., "Cyclin Activation of p34$^{cdc2}$," *Cell, 63*:1013–1024 (1990).

Peng, C–Y., et al., "Mitotic and G$^2$ Checkpoint Control: Regulation of 14–3–3 Protein Binding by Phosphorylation of Cdc25C on Serine–216," *Science, 277*:1501–1505 (1997).

Maleszka, R., et al., "The *Drosophila Melanogaster* dodo (dod) gene, Conserved in Humans, is Functionally Interchangeable with the ESS1 Cell Division gene of *Saccharomyces Cerevisiae,*" *Proc. Natl. Acad. Sci. USA, 93*:447–451 (1996).

Hanes, S.D., et al., "Sequence and Mutational Analysis of ESS1, a Gene Essential for Growth in *Saccharomyces Cerevisiae,*" *Yeast, 5*:55–72 (1989).

Heintz, N., et al., "Regulation of Human Histone Gene Expression: Kinetics of Accumulation and Changes in the Rate of Synthesis and in the Half–Lives of Individual Histone mRNAs During the HeLa Cell Cycle," *Mol. and Cell. Biol., 3*:539–550 (1983).

Davis, F.M., et al., "Monoclonal Antibodies to Mitotic Cells," *Proc. Natl. Acad. Sci. USA, 80*:2926–2930 (1983).

Renzi, L., et al., "MPM–2 Antibody–Reactive Phosphorylations Can be Created in Detergent Extracted Cells by Kinetochore–Bound and Soluble Kinases," *J. Cell Science, 110*:2013–2025 (1997).

Taagepera S., et al., "The MPM–2 Antibody Inhibits Mitogen–Activated Protein Kinase Activity by Binding to an Epitope Containing Phosphothreonine–183," *Mol. Biol. of Cell, 5*:1243–1251 (1994).

Westendorf, J.M., et al., "Cloning of cDNAs for M–Phase Phosphoproteins Recognized by the MPM2 Monoclonal Antibody and Determination of the Phosphorylated Epitope," *Proc. Natl. Acad. Sci. USA, 91*:714–718 (1994).

Kuang, J. and Ashorn, C.L., "At Least Two Kinases Phosphorlate the MPM–2 Epitope During Xenopus Oocyte Maturation," *J. Cell Biol., 123*:(4):859–868 (1993).

Murray, A.W., "Cell Cycle Extracts," Chapter 30, In *Methods Cell Biol, 36* (Academic Press Inc.)pp. 851–605 (1991).

Nicholls, A., et al., "Protein Folding and Association: Insights From the Interfacial and Thermodynamic Properties of Hydrocarbons," *Proteins, 11*:281–296 (1991).

Rudd, K.E., et al., "A New Family of Peptidyl–Prolyl Isomerases," *TIBS, 20*:12–13 (1995).

Schmid, F.X., "Prolyl Isomerases Join the Fold," *Curr. Biol., 5*:993–994 (1995).

Schutkowski, M., et al., "Inhibition of Peptidyl–Prolyl cis/trans Isomerase Activity by Substrate Analog Structures: Thioxo Tetrapeptide–4–Nitroanilides," *Biochemistry, 34*:13016–13026 (1995).

Stukenberg, P.T., et al., "Systematic Identification of Mitotic Phosphoproteins," *Curr. Biol., 7*:338–348 (1997).

Ye X.S., et al., "The NIMA Protein Kinase is Hyperphosphorylated and Activated Downstream of the p34$^{cdc2}$/cyclin B: Coordination of Two mitosis Promoting Kinases," *EMBO J., 14*:968–994 (1995).

Fischer, G., "Peptidyl–Prolyl cis/trans Isomerases and Their Effectors," *Angew. Chem. Int. Ed. Engl., 33*:1415–1436 (1994).

Coleman, R. and Dunphy, W.G., "Cdc2 Regulatory Factors," *Curr. Opin. Biol., 6*:877–882 (1994).

Fischer, G., et al., "Nachweis einer Enzymakatalyse Für die cis–trans–Isomerisierung der Peptidbindung in prolinhaltigen Peptiden," *Biomed. Biochim. Acta., 43*:1101–1111 (1984).

Izumi, T., and Maller, J.L., "Elimination of cdc2 Phosphorylation Sites in the cdc25 Phosphatase Blocks Initiation of M–Phase," *Mol. Biol. of the Cell, 4*:1337–1350 (1993).

Kofron, J.L., et al., "Determination of Kinetic Constants for Peptidyl Prolyl Cis–Trans Isomerases by an Improved Spectrophotometric Assay," *Biochemistry, 30*:6127–6134 (1991).

Kuang, J., et al., "cdc25 Is One of the MPM–2 Antigens Involved in the Activation of Maturation–Promoting Factor," *Mol. Biol. of the Cell., 5*:135–145 (1994).

Rahfeld, J–U., et al., "Confirmation of the Existence of a Third Family Among Peptidyl–Prolyl cis/trans Isomerases. Amino Acid Sequence and Recombinant Production of Parvulin," *FEBS Letters, 352*:180–184 (1994).

Zhao, J–Y., et al., "Theonine Phosphorylation is Associated with Mitosis in HeLa Cells," *FEBS, 249*:389–395 (1989).

Ogg, S., et al., "Purification of a Serine Kinase That Associates With and Phosphorylates Human Cdc25C on Serine 216," *J. Biol Chem., 269*:30461–30469 (1994).

Lu, K.P., et al., "Properties and Regulation of the Cell Cycle–Specific NIMA Protein Kinase of Aspergillus Nidulans," *J. Biol. Chem., 268*:8769–8773 (1993).

Fiol, C.J., et al., "Ordered multisite protein phosphorylation," *Journal of Biological Chemistry, 265*:6061–6065 (1990).

Yaffe, M.B., et al., "The structural basis for 14–3–3: phosphopeptide binding specificity," *Cell, 91*:961–971 (1997).

Yaffe, M.B., et al., "Sequence–specific and phosphorylation– dependent proline isomerization: a potential mitotic regulation mechanism," *Science, 278*:1957–1960 (1997).

Ludwig, H.H., et al., "Synthesis and kinetic properties of various side chain modified peptide derivatives as effectors of prolyl endopeptidase," *Perspective Protein Eng., 10*:1–5 (1996). (From *Chem. Abstracts*, 1997, 126, Abstract No. 340373).

Lindberg, R.A., et al., "Characterization of a human protein threonine kinase isolated by screening an expression library with antibodies to phosphotyrosine," *Oncogene, 8*:351–359 (1993). (From *Chem. Abstracts*, 1993, 118, Abstract No. 186454).

Derwent Publications Ltd., London, GB, "New phospho: peptide(s)—useful as antigen for preparing antibody against paired helical filaments present in brain or patients with Alzheimer's disease," JP 910 146 477 A (Mitsubishi Kasei Corp.), (Feb. 25, 1991). (From Database WPI, Week 451992).

Rotin, D., "WW (WWP) Domains: From Structure to Function," *Curr. Top. Microbiol. Immunol., 228*:115–133, (1998).

Sudol, M., "Structure and Function of the WW Domain," *Prog. Biophys. Mol. Biol., 65*:113–132 (1996).

Macias, M.J., et al., "Structure of the WW domain of a kinase–associated protein complexed with a proline–rich peptide," *Nature, 382*:646–649 (1996).

Shen, M., et al., "The essential mitotic peptidyl–prolyl isomerase Pin1 binds and regulates mitosis–specific phosphoproteins," *Genes & Development, 12*:706–720 (1998).

Pirozzi, G., et al., "Identification of Novel Human WW Domain–containing Proteins by Cloning of Ligand Targets," *J. Biol. Chem., 272*:14611–14616 (1997).

Bedford, M.T., et al., "FBP WW domains and the Abl SH3 domain bind to specific class of proline–rich ligands," *EMBO J., 16*:2376–2383 (1997).

Luise, M., et al., "Dystrophin is phosphorylated by endogenous protein kinases," *Biochem. J., 293*:243–247 (1993).

Shemanko, C.S., et al., "Phosphorylation of the carboxyl terminal region of dystrophin by mitogen–activated protein (MAP) kinase," *Mol. Cell. Biochem. 152*:63–70 (1995).

Dolinski, K., et al., "All cyclophilins and FK506 binding proteins are, individually and collectively, dispensable for viability in *Saccharomyces cerevisiae*," *Proc. Natl. Acad. Sci. USA, 94*:13093–13098 (1997).

Schutkowski, M., et al., "Role of Phosphorylation in Determining the Backbone Dynamics of the Serine/Threonine–Proline Motif and Pin1 Substrate Recognition," *Biochemistry, 37*:5566–5575 (1998).

Izumi, T., et al., "Phosphorylation and Activation of the Xenopus Cdc25 Phosphatase in the Absence of Cdc2 and Cdk2 Kinase Activity," *Mol. Biol. Cell, 6*:215–226 (1995).

Ye, X.S., et al., "The NIMA protein kinase is hyperphosphorylated and activated downstream of $p34^{cdc2}$/cyclin B: coordination of two mitosis promoting kinases," *EMBO J., 14*:986–994 (1995).

* cited by examiner

```
             WW Domain
Pin1/Human   EKLPPGWEKRHSRSSGRVYYFNHITNASQWERPSGNFSS
Ess1/SC      TGLPTPWTVRYSKKREYFFNPETKHSQWEEPEGTNKD
Yap/Human    VPLPAGWEHAKTSS-GQRYFLNHIDQTTTWQDPRKAHLS
Nedd4/Mouse  SPLPPGWEEERQDVL-GRTYYVNHESKRTQWKRPSPDDDL
RSPS/SC      GRLPPGWERRTDNF-GRTYYVDHNTRTTWKRPTLDQTE
Dmd/Human    TSVQGPWERAISPNKVP-YYINHETQTTCWDHPKMTELY
FE65/Rat     SDLPAGWNRVQDTS-G-TYYWNIPTGTYQWEPPGRASPS Consensus    ..LP.GWE.......G....YY.NH.T..T..W..P.
```

*FIG. 6*

SEQUENCE LISTING

<160> NUMBER OF SEQ ID NOS: 42

<210> SEQ ID NO 1
<211> LENGTH: 31
<212> TYPE: PRT
<213> ORGANISM: Homo sapien

<400> SEQUENCE: 1

Leu Pro Pro Gly Trp Glu Lys Arg Met Ser Arg Ser Ser Gly Arg Val
 1               5                  10                  15

Tyr Tyr Phe Asn His Thr Thr Asn Ala Ser Gln Trp Glu Arg Pro
            20                  25                  30

<210> SEQ ID NO 2
<211> LENGTH: 31
<212> TYPE: PRT
<213> ORGANISM: Unknown
<220> FEATURE:
<223> OTHER INFORMATION: synthetic peptide

<400> SEQUENCE: 2

Leu Pro Thr Pro Trp Thr Val Arg Tyr Ser Lys Ser Lys Arg Glu
 1               5                  10                  15

Tyr Phe Phe Asn Pro Glu Thr Lys His Ser Gln Trp Glu Glu Pro
            20                  25                  30

<210> SEQ ID NO 3
<211> LENGTH: 30
<212> TYPE: PRT
<213> ORGANISM: mouse

<400> SEQUENCE: 3

Leu Pro Pro Gly Trp Glu Glu Lys Gln Asp Asp Arg Gly Arg Ser Tyr
 1               5                  10                  15

Tyr Val Asp His Asn Ser Lys Thr Thr Thr Trp Ser Lys Pro
            20                  25                  30

<210> SEQ ID NO 4
<211> LENGTH: 30
<212> TYPE: PRT
<213> ORGANISM: Homo sapien

<400> SEQUENCE: 4

Val Gln Gly Pro Trp Glu Arg Ala Ile Ser Pro Asn Lys Val Pro Tyr
 1               5                  10                  15

Tyr Thr Asn His Glu Thr Gln Thr Thr Cys Trp Asp His Pro
            20                  25                  30

<210> SEQ ID NO 5
<211> LENGTH: 30
<212> TYPE: PRT
<213> ORGANISM: mouse

<400> SEQUENCE: 5

Ala Lys Ser Met Trp Thr Glu His Lys Ser Pro Asp Gly Arg Thr Tyr
 1               5                  10                  15

Tyr Tyr Asn Thr Glu Thr Lys Gln Ser Thr Trp Glu Lys Pro
            20                  25                  30

<210> SEQ ID NO 6
<211> LENGTH: 29

```
<212> TYPE: PRT
<213> ORGANISM: rat

<400> SEQUENCE: 6

Leu Pro Ala Gly Trp Met Arg Val Gln Asp Thr Ser Gly Thr Tyr Tyr
 1               5                  10                  15

Trp His Ile Pro Thr Gly Thr Thr Gln Trp Glu Pro Pro
            20                  25

<210> SEQ ID NO 7
<211> LENGTH: 30
<212> TYPE: PRT
<213> ORGANISM: mouse

<400> SEQUENCE: 7

Leu Pro Ala Gly Trp Glu Met Ala Lys Thr Ser Ser Gly Gln Arg Tyr
 1               5                  10                  15

Phe Leu Asn His Ile Asp Gln Thr Thr Thr Trp Gln Asp Pro
            20                  25                  30

<210> SEQ ID NO 8
<211> LENGTH: 8
<212> TYPE: PRT
<213> ORGANISM: synthetic peptide
<220> FEATURE:
<221> NAME/KEY: PHOSPHORYLATION
<222> LOCATION: (4)...(4)

<400> SEQUENCE: 8

Trp Phe Tyr Ser Pro Phe Leu Glu
 1               5

<210> SEQ ID NO 9
<211> LENGTH: 8
<212> TYPE: PRT
<213> ORGANISM: synthetic peptide

<400> SEQUENCE: 9

Trp Phe Tyr Ser Pro Phe Leu Glu
 1               5

<210> SEQ ID NO 10
<211> LENGTH: 10
<212> TYPE: PRT
<213> ORGANISM: synthetic peptide
<220> FEATURE:
<221> NAME/KEY: PHOSPHORYLATION
<222> LOCATION: (5)...(5)

<400> SEQUENCE: 10

Glu Gln Pro Leu Thr Pro Val Thr Asp Leu
 1               5                  10

<210> SEQ ID NO 11
<211> LENGTH: 10
<212> TYPE: PRT
<213> ORGANISM: synthetic peptide

<400> SEQUENCE: 11

Glu Gln Pro Leu Thr Pro Val Thr Asp Leu
 1               5                  10

<210> SEQ ID NO 12
<211> LENGTH: 10
```

```
<212> TYPE: PRT
<213> ORGANISM: synthetic peptide

<400> SEQUENCE: 12

Ile Pro Gly Thr Pro Pro Asn Tyr Asp
1               5

<210> SEQ ID NO 13
<211> LENGTH: 9
<212> TYPE: PRT
<213> ORGANISM: synthetic peptide
<220> FEATURE:
<221> NAME/KEY: PHOSPHORYLATION
<222> LOCATION: (4)...(4)

<400> SEQUENCE: 13

Trp Phe Tyr Ser Pro Arg Leu Lys Lys
1               5

<210> SEQ ID NO 14
<211> LENGTH: 9
<212> TYPE: PRT
<213> ORGANISM: synthetic peptide

<400> SEQUENCE: 14

Trp Phe Tyr Ser Pro Arg Leu Lys Lys
1               5

<210> SEQ ID NO 15
<211> LENGTH: 14
<212> TYPE: PRT
<213> ORGANISM: synthetic peptide

<400> SEQUENCE: 15

Asp Ala Gly Leu Lys Glu Ser Pro Leu Gln Thr Pro Thr Glu
1               5                   10

<210> SEQ ID NO 16
<211> LENGTH: 13
<212> TYPE: PRT
<213> ORGANISM: synthetic peptide

<400> SEQUENCE: 16

Thr Arg Ile Pro Ala Lys Thr Pro Pro Ala Pro Lys Thr
1               5                   10

<210> SEQ ID NO 17
<211> LENGTH: 14
<212> TYPE: PRT
<213> ORGANISM: synthetic peptide

<400> SEQUENCE: 17

Gly Tyr Ser Ser Pro Gly Ser Pro Gly Thr Pro Gly Ser Arg
1               5                   10

<210> SEQ ID NO 18
<211> LENGTH: 13
<212> TYPE: PRT
<213> ORGANISM: synthetic peptide

<400> SEQUENCE: 18

Ser Arg Ser Arg Thr Pro Ser Leu Pro Thr Pro Pro Thr
1               5                   10
```

```
<210> SEQ ID NO 19
<211> LENGTH: 13
<212> TYPE: PRT
<213> ORGANISM: synthetic peptide

<400> SEQUENCE: 19

Lys Val Ala Val Val Arg Thr Pro Pro Lys Ser Pro Ser
 1               5                  10

<210> SEQ ID NO 20
<211> LENGTH: 14
<212> TYPE: PRT
<213> ORGANISM: synthetic peptide

<400> SEQUENCE: 20

Lys Val Ala Val Val Arg Thr Ile Pro Pro Lys Ser Pro Ser
 1               5                  10

<210> SEQ ID NO 21
<211> LENGTH: 14
<212> TYPE: PRT
<213> ORGANISM: synthetic peptide

<400> SEQUENCE: 21

Val Arg Thr Pro Pro Lys Ser Pro Ser Ser Ala Lys Ser Arg
 1               5                  10

<210> SEQ ID NO 22
<211> LENGTH: 13
<212> TYPE: PRT
<213> ORGANISM: synthetic peptide

<400> SEQUENCE: 22

Val Gln Ser Lys Ile Gly Ser Leu Asp Asn Ile Thr His
 1               5                  10

<210> SEQ ID NO 23
<211> LENGTH: 13
<212> TYPE: PRT
<213> ORGANISM: synthetic peptide

<400> SEQUENCE: 23

Gly Ser Leu Asp Asn Ile Thr His Val Pro Gly Gly Gly
 1               5                  10

<210> SEQ ID NO 24
<211> LENGTH: 13
<212> TYPE: PRT
<213> ORGANISM: synthetic peptide

<400> SEQUENCE: 24

Thr Ser Pro Arg His Leu Ser Asn Val Ser Ser Thr Gly
 1               5                  10

<210> SEQ ID NO 25
<211> LENGTH: 16
<212> TYPE: PRT
<213> ORGANISM: synthetic peptide

<400> SEQUENCE: 25

Pro Arg His Leu Ser Asn Val Ser Ser Thr Gly Ser Ile Asp Met Val
 1               5                  10                  15

<210> SEQ ID NO 26
<211> LENGTH: 16
```

```
<212> TYPE: PRT
<213> ORGANISM: synthetic peptide

<400> SEQUENCE: 26

Pro Arg His Leu Ser Asn Val Ser Ser Thr Gly Ser Ile Asp Met Val
1               5                   10                  15

<210> SEQ ID NO 27
<211> LENGTH: 13
<212> TYPE: PRT
<213> ORGANISM: synthetic peptide

<400> SEQUENCE: 27

Asn Val Ser Ser Thr Gly Ser Ile Asp Met Val Asp Ser
1               5                   10

<210> SEQ ID NO 28
<211> LENGTH: 13
<212> TYPE: PRT
<213> ORGANISM: synthetic peptide

<400> SEQUENCE: 28

Ser Ile Asp Met Val Asp Ser Pro Gln Leu Ala Thr Leu
1               5                   10

<210> SEQ ID NO 29
<211> LENGTH: 13
<212> TYPE: PRT
<213> ORGANISM: synthetic peptide

<400> SEQUENCE: 29

Lys Val Ala Val Val Arg Thr Pro Pro Lys Ser Pro Ser
1               5                   10

<210> SEQ ID NO 30
<211> LENGTH: 13
<212> TYPE: PRT
<213> ORGANISM: synthetic peptide

<400> SEQUENCE: 30

Lys Val Ala Val Val Arg Thr Pro Pro Lys Ser Pro Ser
1               5                   10

<210> SEQ ID NO 31
<211> LENGTH: 15
<212> TYPE: PRT
<213> ORGANISM: synthetic peptide

<400> SEQUENCE: 31

Lys Glu Val Asp Ala Ala Val Thr Pro Glu Glu Arg His Leu Ser
1               5                   10                  15

<210> SEQ ID NO 32
<211> LENGTH: 15
<212> TYPE: PRT
<213> ORGANISM: synthetic peptide

<400> SEQUENCE: 32

Lys Glu Val Asp Ala Ala Val Thr Pro Glu Glu Arg His Leu Ser
1               5                   10                  15

<210> SEQ ID NO 33
<211> LENGTH: 39
<212> TYPE: PRT
<213> ORGANISM: Homo sapien
```

-continued

```
<400> SEQUENCE: 33

Glu Lys Leu Pro Pro Gly Trp Glu Lys Arg Met Ser Arg Ser Ser Gly
 1               5                  10                  15

Arg Val Tyr Tyr Phe Asn His Ile Thr Asn Ala Ser Gln Trp Glu Arg
            20                  25                  30

Pro Ser Gly Asn Ser Ser Ser
        35

<210> SEQ ID NO 34
<211> LENGTH: 39
<212> TYPE: PRT
<213> ORGANISM: Unknown
<220> FEATURE:
<223> OTHER INFORMATION: synthetic peptide

<400> SEQUENCE: 34

Thr Gly Leu Pro Thr Pro Trp Thr Val Arg Tyr Ser Lys Ser Lys Lys
 1               5                  10                  15

Arg Glu Tyr Phe Phe Asn Pro Glu Thr Lys His Ser Gln Trp Glu Glu
            20                  25                  30

Pro Glu Gly Thr Asn Lys Asp
        35

<210> SEQ ID NO 35
<211> LENGTH: 38
<212> TYPE: PRT
<213> ORGANISM: Homo sapien

<400> SEQUENCE: 35

Val Pro Leu Pro Ala Gly Trp Glu Met Ala Lys Thr Ser Ser Gly Gln
 1               5                  10                  15

Arg Tyr Phe Leu Asn His Ile Asp Gln Thr Thr Thr Trp Gln Asp Pro
            20                  25                  30

Arg Lys Ala Met Leu Ser
        35

<210> SEQ ID NO 36
<211> LENGTH: 38
<212> TYPE: PRT
<213> ORGANISM: mouse

<400> SEQUENCE: 36

Ser Pro Leu Pro Pro Gly Trp Glu Glu Arg Gln Asp Val Leu Gly Arg
 1               5                  10                  15

Thr Tyr Tyr Val Asn His Glu Ser Arg Arg Thr Gln Trp Lys Arg Pro
            20                  25                  30

Ser Pro Asp Asp Asp Leu
        35

<210> SEQ ID NO 37
<211> LENGTH: 38
<212> TYPE: PRT
<213> ORGANISM: Unknown
<220> FEATURE:
<223> OTHER INFORMATION: synthetic peptide

<400> SEQUENCE: 37

Gly Arg Leu Pro Pro Gly Trp Glu Arg Arg Thr Asp Asn Phe Gly Arg
 1               5                  10                  15
```

```
Thr Tyr Tyr Val Asp His Asn Thr Arg Thr Thr Thr Trp Lys Arg Pro
                20                  25                  30

Thr Leu Asp Gln Thr Glu
         35
```

<210> SEQ ID NO 38
<211> LENGTH: 38
<212> TYPE: PRT
<213> ORGANISM: Homo sapien

<400> SEQUENCE: 38

```
Thr Ser Val Gln Gly Pro Trp Glu Arg Ala Ile Ser Pro Asn Lys Val
 1               5                  10                  15

Pro Tyr Tyr Ile Asn His Glu Thr Gln Thr Thr Cys Trp Asp His Pro
                20                  25                  30

Lys Met Thr Glu Leu Tyr
         35
```

<210> SEQ ID NO 39
<211> LENGTH: 37
<212> TYPE: PRT
<213> ORGANISM: rat

<400> SEQUENCE: 39

```
Ser Asp Leu Pro Ala Gly Trp Met Arg Val Gln Asp Thr Ser Gly Thr
 1               5                  10                  15

Tyr Tyr Trp His Ile Pro Thr Gly Thr Thr Gln Trp Glu Pro Pro Gly
                20                  25                  30

Arg Ala Ser Pro Ser
         35
```

<210> SEQ ID NO 40
<211> LENGTH: 31
<212> TYPE: PRT
<213> ORGANISM: Unknown
<220> FEATURE:
<223> OTHER INFORMATION: synthetic peptide
<221> NAME/KEY: VARIANT
<222> LOCATION: (1)...(31)
<223> OTHER INFORMATION: Xaa = Any Amino Acid
<221> NAME/KEY: MOD_RES
<222> LOCATION: (14)...(14)
<223> OTHER INFORMATION: turn like or polar residue
<221> NAME/KEY: MOD_RES
<222> LOCATION: (16)...(16)
<223> OTHER INFORMATION: Tyrosine/Phenylalnine
<221> NAME/KEY: MOD_RES
<222> LOCATION: (17)...(17)
<223> OTHER INFORMATION: Tyrosine/Phenylalanine
<221> NAME/KEY: MOD_RES
<222> LOCATION: (18)...(18)
<223> OTHER INFORMATION: Hydrophobic Amino Acid
<221> NAME/KEY: MOD_RES
<222> LOCATION: (19)...(19)
<223> OTHER INFORMATION: Asparagine/Aspartic Acid
<221> NAME/KEY: MOD_RES
<222> LOCATION: (22)...(22)
<223> OTHER INFORMATION: Threonine/Serine
<221> NAME/KEY: MOD_RES
<222> LOCATION: (23)...(23)
<223> OTHER INFORMATION: Turn like or polar residue
<221> NAME/KEY: MOD_RES
<222> LOCATION: (25)...(25)
<223> OTHER INFORMATION: Threonine/Serine
<221> NAME/KEY: MOD_RES
<222> LOCATION: (26)...(26)
<223> OTHER INFORMATION: Turn like or polar residue
<221> NAME/KEY: MOD_RES
<222> LOCATION: (29)...(29)

```
<223> OTHER INFORMATION: Turn like or polar residue
<221> NAME/KEY: MOD_RES
<222> LOCATION: (31)...(31)
<223> OTHER INFORMATION: Turn like or polar residue

<400> SEQUENCE: 40

Leu Xaa Xaa Gly Trp Thr Xaa Xaa Xaa Xaa Xaa Gly Xaa Xaa Xaa
 1               5                  10                  15

Xaa Xaa Xaa His Xaa Xaa Xaa Xaa Thr Xaa Trp Xaa Xaa Pro Xaa
            20                  25                  30

<210> SEQ ID NO 41
<211> LENGTH: 31
<212> TYPE: PRT
<213> ORGANISM: Unknown
<220> FEATURE:
<223> OTHER INFORMATION: synthetic peptide
<221> NAME/KEY: VARIANT
<222> LOCATION: (1)...(31)
<223> OTHER INFORMATION: Xaa = Any Amino Acid

<400> SEQUENCE: 41

Leu Pro Xaa Gly Trp Glu Xaa Xaa Xaa Xaa Xaa Xaa Gly Xaa Xaa
 1               5                  10                  15

Tyr Tyr Xaa Asn His Xaa Thr Xaa Xaa Thr Xaa Trp Xaa Xaa Pro
            20                  25                  30

<210> SEQ ID NO 42
<211> LENGTH: 14
<212> TYPE: PRT
<213> ORGANISM: Unknown
<220> FEATURE:
<223> OTHER INFORMATION: synthetic peptide

<400> SEQUENCE: 42

Leu Pro Gly Trp Glu Gly Tyr Tyr Asn His Thr Thr Trp Pro
 1               5                  10
```

METHODS AND COMPOSITIONS FOR REGULATING PROTEIN-PROTEIN INTERACTIONS

GOVERNMENT SUPPORT

The invention was supported, in whole or in part, by grant R01 GM56230 from the National Institutes of Health. The Government has certain rights in the invention.

BACKGROUND OF THE INVENTION

Homeostasis of the organism depends upon interactions between protein-interacting modules and ligands to activate and deactivate cell signaling pathways for biological processes such as cell proliferation, cell death and protein degradation. Protein-interacting modules are conserved regions of amino acids that bind specific sequences in target proteins or position enzymes in close proximity to their substrates. For example, src homology domain 2 (SH2) binds phosphotyrosine residues on target cells to mediate receptor activation and receptor-ligand binding (Pawson, T., et al., Science 278:2075 (1997)). An example are WW-domains which are highly conserved regions of approximately 40 amino acids residues with two invariant tryptophans (W) in a triple stranded β sheet (Sudol, M. Prog. Biophys. Mol. Biol. 65:113 (1996); Rotin, D. Curr. Topics Microbiol. Immunol. 228:115 (1998)). Although the WW-domains of certain polypeptides have been implicated in protein-protein interactions by binding to proline rich sequences, many of their ligands do not contain proline rich sequences. (Sudol, M. Prog. Biophys. Mol. Biol. 65:113 (1996); Staub, O. et al., Structure 4:495 (1996), Rotin, D., Curr. Top. Microbiol. Immunol. 228:115 (1998)). Therefore, the role of WW-domain-containing proteins in mediating cell signaling events in biological processes is not known. However, due to their potential importance in cellular processes, it is important to elucidate a clearer understanding of the role of WW-domains in protein-protein interactions and cell signaling.

SUMMARY OF THE INVENTION

The present invention is based upon the discovery that WW-domains are phosphoserine or phosphothreonine binding modules. As further described herein, the present invention is also based upon the discovery that the WW-domain itself is phosphorylated, and that phosphorylation/dephosphorylation of the WW-domain polypeptide regulates the interaction of the WW-domain polypeptide with its phosphorylated ligand. As a result of this discovery, methods and compositions are available to modulate protein-protein interactions, e.g., the interaction between a signaling or regulatory polypeptide and its phosphorylated ligands.

The invention relates to methods of modulating protein-protein interactions comprising modulating the binding of WW-domain polypeptides with phosphorylated ligands. In one embodiment the binding interaction between the WW-domain containing polypeptide and phosphorylated ligand is inhibited. In another embodiment the binding interaction of the WW-domain containing polypeptide and phosphorylated ligand is enhanced. As used herein, a phosphorylated ligand is a molecule (e.g., protein, peptide, peptide mimetic or small organic molecule) containing a phosphoserine or phosphothreonine that binds to a WW-domain containing polypeptide. For example, ligands specifically encompassed by the present invention include tau protein, amyloid precursor protein, Cdc25C, Cdc27, Plk1, NIMA, Myt1, Rab4, Wee1, Mos, Sox3, Xbr1b, MP75 (E-MAP-115), MP110 (Cdc5), MP68, and MP30. WW-domain containing polypeptides specifically encompassed by the present invention include Pin1, NEDD4, YAP, FE65, formin binding protein, dystrophin, utropin, Ess1p/Ptf1p, Rsp5, Pub1, Dodo, Msb1, ORF1, YKB2, DP71, C38D4.5, P9659.21, Yo61, Yfx1, ZK1248.15, KO15c11, CD45AP, FBP11, FBP21, FBP23, FBP28 and FBP30.

Also encompassed by the present invention are molecules which mimic a WW-domain, referred to herein as WW-domain mimic molecules or pseudo-WW-domain molecules. Such molecules possess structural similarity with the WW-domains described herein or contain the consensus sequence $LxxGWtx_6Gtx(Y/F)(Y/F)h(N/D)Hx(T/S)tT(T/S)tWxtPt$ SEQ ID NO: 40 (where x=any amino acid, t=turn like or polar residue, and h=hydrophobic amino acid as described by Rotin, D., Curr. Top. Microbiol. Immunol. 228:115–133 (1998) the teachings of which are incorporated herein by reference in their entirety). For example, a WW-domain can contained the consensus sequence $LP_xG\text{-}WE_{xxxxxxx}G_{xx}YY_xNH_xT_{xx}T_xW_{xx}P$ SEQ ID NO: 41, where x=any amino acid. The WW-domain mimic molecules are amino acid sequences, peptides, peptide mimetics, or polypeptides. The WW-domain mimic molecules are capable of interacting with, or binding to, phosphoserine/phosphothreonine ligands, thus modulating the activity of the phosphorylated ligand.

Also encompassed by the present invention are phosphorylated ligand sequences, referred to herein as phosphorylated ligand mimics, or phosphorylated pseudo-ligands. Phosphorylated ligand mimics are amino acid sequences, peptides, peptide mimetics, or polypeptides that contain a phosphoserine or phosphothreonine residue(s) and are of sufficient length and share sufficient amino acid identity with the ligand that the ligand mimics and interacts with, or binds to, the WW-domain containing polypeptide and thus modulates the activity of the WW-domain containing polypeptide.

A method of modulating the activity of a phosphorylated ligand or ligand mimic for a WW-domain, or a WW-domain containing polypeptide, comprises providing a WW-domain or WW-domain mimic which interacts with the ligand, wherein the activity of the phosphorylated ligand, ligand mimic, WW-domain polypeptide or WW-domain mimic is modulated (e.g., inhibited or enhanced). The activity can be binding activity between the ligand and WW-domain; enzymatic/regulatory activity of the WW-domain polypeptide; or both. For example, the prolyl-peptidyl cis-trans isomerase activity of Pin1 or ubiquitin ligase activity of Nedd4 can increase following binding of the WW-domain to a phosphorylated ligand.

Another aspect of the invention relates to regulating cell growth comprising mediating the binding of the WW-domain of Pin1 to a mitotic regulatory protein. The WW-domain can bind to a phosphorylated ligand (e.g., NIMA) resulting in cell proliferation. Cell proliferation can be regulated by regulating the phosphorylation state of the WW-domain. Dephosphorylation of the WW-domain of Pin1 leads to binding of the WW-domain to a phosphorylated ligand resulting in cell proliferation. Likewise, phosphorylation of the WW-domain inhibits binding to phosphorylated ligands resulting in cell death.

The invention also encompasses methods of regulating neurodegenerative diseases by modulating the interaction of a WW-domain and a ligand in cells (e.g., neurons, glial cells, Schwann cells) of the central (e.g., brain and spinal cord) and peripheral nervous system and any cells associated with the central or peripheral nervous systems (e.g., skeletal muscle). The interaction between the WW-domain and a neural cellular target can inhibit, halt, prevent or reverse neural degeneration by, for example, interfering with neuronal cell death (e.g., apoptosis, necrosis) or restoring neuronal function.

A further aspect of the invention encompasses a method of regulating the function of phosphorylated ligands of WW-domain containing polypeptides comprising mediating the binding of the ligand to the WW-domain. Specifically encompassed by the invention is a method of regulating the activity of hyperphosphorylated tau protein in Alzheimer's disease comprising enhancing the binding of the WW-domain of Pin1 to the phosphorylated threonine 231 of tau whereby the binding of the WW-domain to tau results in binding of tau to microtubules leading to microtubule assembly. Another method of the invention relates to a method of regulating the interaction between the WW-domain of dystrophin and phosphorylated ligands.

The present invention further relates to a method of identifying a substance that modulates the interaction of a WW-domain containing polypeptide and a ligand, wherein the ligand is a phosphoserine or phosphothreonine ligand comprising contacting the WW-domain containing polypeptide with one, or more, test substances; maintaining the test substances and the WW-domain containing polypeptide under conditions suitable for interaction; and determining the interaction between the test substance and WW-domain containing polypeptide, wherein the interaction indicates that the test substance modulates the interaction between the WW-domain-containing polypeptide and the ligand. In one embodiment the interaction between the WW-domain and ligand that is modulated by the test substance is binding interaction. In another embodiment the interaction is enzymatic activity, in particular prolyl-peptidyl cis-trans isomerase activity of Pin1 or the ubiquitin ligase activity of Nedd4. The binding interaction or enzymatic activity between the WW-domain and ligand can be increased or decreased in the presence of the test substance. Thus, the test substance can be an antagonist or agonist of the interaction between the WW-domain and the ligand.

The present invention also provides mutants of WW-domain containing polypeptides comprising at least one mutation in the WW-domain. The ability of the mutant WW-domain containing polypeptides to bind a ligand is altered. In one embodiment the binding ability is enhanced. In another embodiment the binding ability is reduced. The mutant WW-domain containing polypeptides can also have altered enzymatic, catalytic or regulatory activity. In one embodiment the enzymatic activity of the WW-domain containing polypeptide is enhanced. In another embodiment the enzymatic activity is reduced. The mutant can have a mutation comprising a modification of an amino acid wherein the amino acid is selected from the group consisting of tyrosine at position 23, tryptophan at position 34, arginine at position 14, serine at position 16, serine at position 18 in Pin1, or equivalent positions in other WW-domain-containing proteins. The modified amino acid is replaced with an amino acid residue selected from the group consisting of alanine, glutamic acid or phenylalanine.

The invention also relates to a method of regulating protein degradation comprising regulating the phosphorylation of a serine residue of a WW-domain polypeptide. In particular, the WW-domain containing polypeptide is the ubiquitin ligase Nedd4. In one embodiment phosphorylation of the serine residue leads to binding of the WW-domain containing polypeptide and ligand to initiate polypeptide degradation. In another embodiment dephosphorylation of the serine residue of the WW-domain containing polypeptide prevents binding of the WW-domain containing polypeptide and ligand thereby preventing polypeptide degradation. The regulation of protein degradation by the methods of the invention can result in regulation of cell growth. In yet another embodiment modulations in the protein degradation lead to regulation of cell growth. In particular, inhibition of Cdc25 degradation by the ubiquitin pathway results in cell death.

In yet another aspect of the invention relates to a method of treating a WW-domain containing polypeptide-mediated condition in a mammal, wherein the condition results from an alteration in a ligand for the WW-domain containing polypeptide, wherein the ligand is a phosphoserine or phosphothreonine ligand comprising introducing into the mammal an amount of a WW-domain containing polypeptide effective to regulate the ligand, thereby alleviating the condition.

In another embodiment the present invention relates to a method of treating a WW-domain containing polypeptide-mediated condition in a mammal, wherein the condition results from an alteration in the WW-domain containing polypeptide wherein a ligand for the WW-domain contains a phosphoserine or phosphothreonine, comprising introducing into the mammal an amount of a WW-domain containing polypeptide effective to alleviate the condition.

The invention further relates to a method of delivering a drug to treat a condition in a mammal, wherein the condition results from an alteration in a phosphorylated ligand for a WW-domain containing polypeptide, comprising combining the drug and the WW-domain containing polypeptide or a fragment under conditions suitable to form a complex; and administering the complex to the mammal, wherein the complex and phosphorylated ligand interact thereby alleviating the condition.

The inventions which are described herein provide compositions and methods to modulate protein-protein interactions such as binding interactions between signaling or regulatory proteins and their phosphorylated ligands. The methods permit inhibiting or enhancing the interaction between a WW-domain containing polypeptide and its phosphorylated ligand. The methods described herein can be used for regulating cell growth; targeting proteins for cellular degradation; restoring the function of tau to bind microtubules and promote or restore microtubule assembly in neurodegenerative diseases such as Alzheimer's disease, Dementia pugilistica, Down's syndrome, Parkinson's disease, Pick's disease; identifying a substance which alters the interaction of WW-domain containing polypeptides and their phosphorylated ligands; and targeting drugs to ligands of WW-domain containing polypeptides to treat disease conditions in a mammal. The methods provide a means to assess the interaction of a phosphoserine/phosphothreonine binding module (WW-domain containing polypeptide) and its cellular ligands.

The top and bottom lines illustrate the X-ray structural elements in native Pin 1 and the NMR structural elements in the isolated YAP WW-domain, respectively. The black boxes with white letter define the residues in the Pin1 WW-domain, whose mutations affected the interactions with phosphoproteins. White boxes with black letters define the residues whose mutations had no detectable effect. The numbers above the sequences refer to human Pin 1 sequence.

Figure 3:
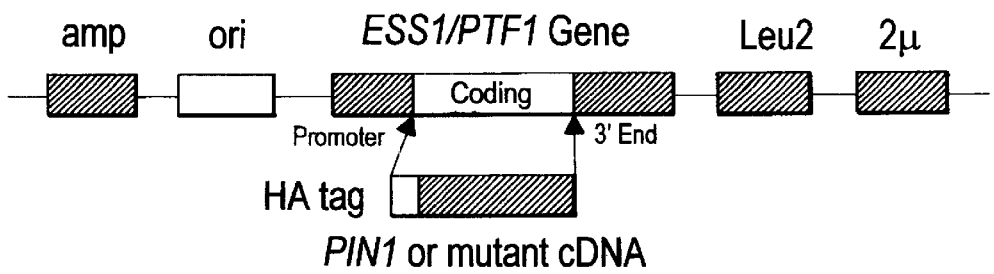

FIG. 3 depicts the coding sequence of a fully functional PTF1 genomic fragment replaced with Pin1 or its mutant cDNAs in a YEP vector. An HA tag was added at the N-terminus to detect protein expression.

Figure 4B:
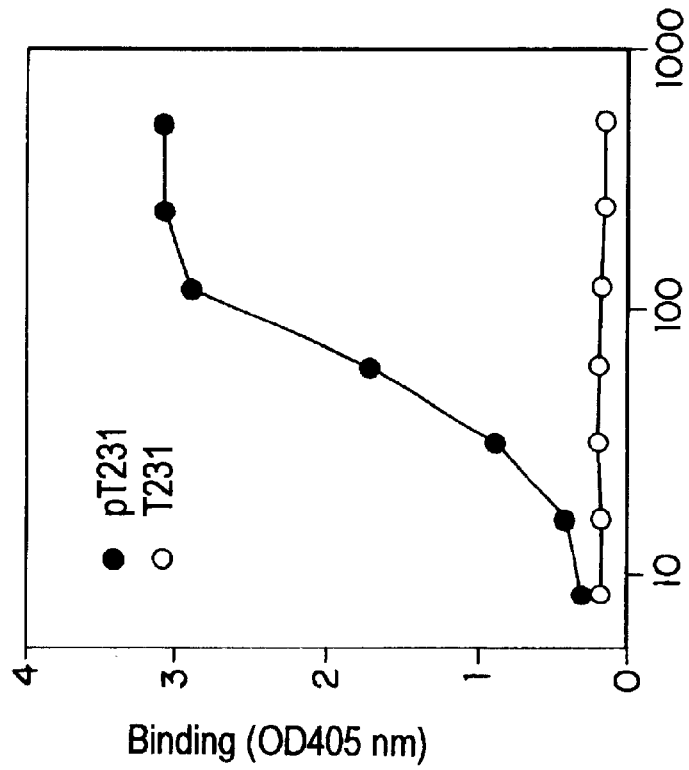
Figure 4A:
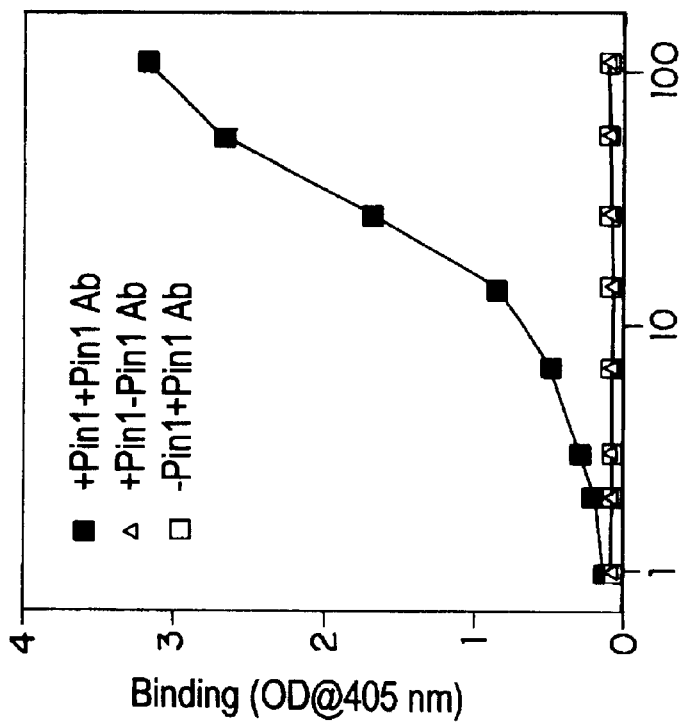

FIG. 4A is a graphic representation of the binding affinity of Pin1 to tau peptides detected by an enzyme linked immunoabsorbant assay using Pin1 antibodies (Pin1 Ab).

FIG. 4B is a graphic representation of the binding affinity of Pin1 and phosphorylated (pT231) or nonphosphorylated (T231) tau peptide.

Figure 5A:
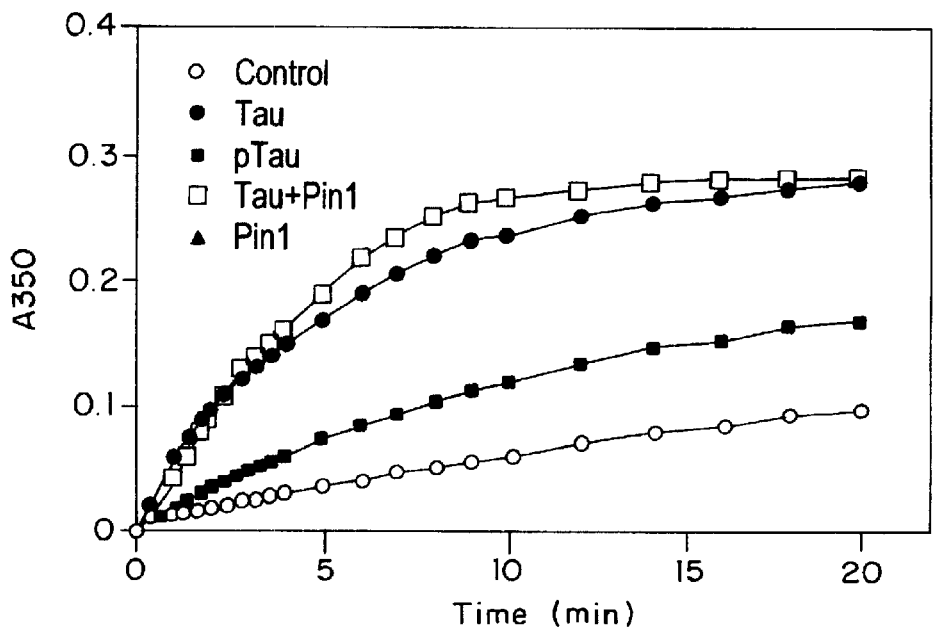

FIG. 5A is a graphic representation of the inability of Pin1 to affect tau induced tubulin assembly.

Figure 5B:
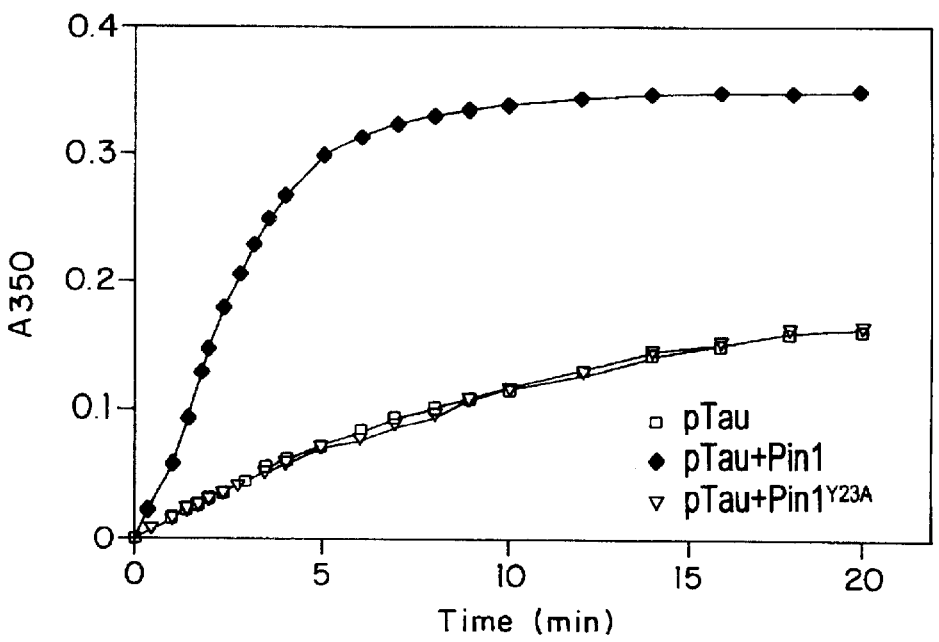

FIG. 5B is a graphic representation of the ability of phosphorylated Tau (pTau) to microtubules assembly in the presence of Pin 1, but not the Pin1$^{Y23A}$ mutant.

FIG. 6 depicts the amino acid sequence of the WW-domain of Pin1/human (SEQ ID NO: 33), beginning with the sixth amino acid; ESS1/9C (SEQ ID NO: 34); Yap/Human (SEQ ID NO: 35); Nedd4/Mouse (SEQ ID NO: 36); RSPS/9C (SEQ ID NO: 37); Dmd/human (SEQ ID NO: 38) and FE65/Rat (SEQ ID NO: 39) Consensus (SEQ ID NO: 42).

DETAILED DESCRIPTION OF THE INVENTION

The present invention relates to the discovery that WW-domains bind serine or threonine phosphoproteins, polypeptides, or peptides with high affinity in a phosphate dependent manner. The WW-domain-containing serine or threonine phosphorylated binding polypeptides of the present invention inhibit dephosphorylation of ligands when bound to the ligand. Binding of the WW-domain containing polypeptide to a ligand can alter the activity of the WW-domain containing polypeptide, ligand or both.

The term "WW-domain containing polypeptide" as used herein refers to a protein (also referred to herein as a polypeptide) which binds phosphorylated ligands. For example, the WW-domain-containing polypeptides encompassed by the present invention include Pin1, Nedd4, YAP, FE65, formin binding protein, dystrophin, utropin and Ess1p/Ptf1p, Rsp5, Pub1, Dodo, Msb1, ORF1, YKB2, DP71, C38D4.5, P9659.21, Yo61, Yfx1, ZK1248.15, KO15c11, CD45AP, FBP11, FBP21, FBP23, FBP28 and FBP30. (Rotin, D. *Curr. Topics Microbiol. Immunol.* 228:115 (1998)). Database accession numbers for the nucleotide and amino acid sequences for these WW-domain-containing proteins are known. (Rotin, D. *Curr. Topics Microbiol. Immunol.* 228:115 (1998)). It is understood that any additional WW-domain-containing proteins to be discovered are within the scope of the invention.

"WW-domain-containing polypeptide", as the term is used herein, can also include any polypeptide which shows sequence and structural identity to a WW-domain which contains an amino acid sequence with identity to any known WW-domain containing polypeptides such as Pin1, Nedd4, YAP, FE65, formin binding protein, dystropin, utropin, Ess1p/Ptf1p, Rsp5, Pub1, Dodo, Msb1, ORF1, YKB2, DP71, C38D4.5, P9659.21, Yo61, Yfx1, ZK1248.15, KO15c11, CD45AP, FBP11, FBP21, FBP23, FBP28 and FBP30. (FIG. 6) (See, for example, Hunter, T., et al., WO 97/17986 (1997); Rotin, D., *Curr. Top. Microbiol. Immunol.* 228:115–133 (1998), the teachings of which are incorporated herein in their entirety). Sequence identity can be determined using database search strategies well known in the art including, for example, Basic Local Alignment Search Tool (BLAST) (Altschul, S. F., et al., *J Mol. Biol.* 215:403–410 (1990)) and FASTA (Pearson, W. R., et al., *Proc. Natl. Acad. Sci. U.S.A.* 85:2444–2448 (1988)) algorithms. In one embodiment, the BLAST parameters are set such that they yield a sequence having at least about 60% sequence identity with the corresponding known WW-domain sequence, preferably, at least about 70% sequence. In another embodiment, the percent sequence identity is at least about 85%, and in yet another embodiment, at least about 95%. Such molecules are also referred to herein as WW-domain mimic molecules and are characterized by highly conserved regions of approximately 40 amino acids residues with two invariant tryptophans (W) in a triple stranded β sheet (Sudol, M. *Prog. Biophys. Mol. Biol.* 65:113 (1996); Rotin, D. *Curr. Topics Microbiol. Immunol.* 228:115 (1998)). Thus, the WW-domain mimic molecules possess structural similarity with the WW-domains described herein or contain the consensus sequence LxxGWtx$_6$Gtx(Y/F)(Y/F)h(N/D)Hx(T/S)tT(T/S)tWxtPt (where x=any amino acid, t=turn like or polar residue, and h=hydrophobic amino acid as described by Rotin, D., *Curr. Top. Microbiol. Immunol.* 228:115–133 (1998)). For example, the WW-domain of a WW-domain mimic molecule can have the consensus sequence LP$_x$GWE$_{xxxxxxx}$G$_{xx}$YY$_x$NH$_x$T$_{xx}$T$_{xx}$P, where $_x$=any amino acid. (FIG. 6). The WW-domain mimic molecules can be about 38–40 amino acids in length, or they can be shorter or longer than 38–40 amino acids. The WW-domain mimic molecules are capable of interacting with, or binding to, phosphoserine/phosphothreonine ligands, thus modulating the activity of the phosphorylated ligand.

It is also envisioned that any WW-domain or WW-domain containing polypeptide functionally equivalent to the molecules described herein will be within the scope of the invention. The phrase "functionally equivalent" as used herein refers to any molecule (e.g., polypeptide and nucleic acid sequence encoding the polypeptide) which mimics the interaction (e.g., binding, enzymatic activity) of the WW-domain or WW-domain containing polypeptides described herein (such as Pin1, Nedd4) or which exhibit nucleotide or amino acid sequence identity to WW-domain containing polypeptides such as Pin1 or Nedd4, for example. The nucleotide and deduced amino acid of Pin1 is known. (See Hunter, T., et al., WO 97/17986, (1997), the teachings of which are incorporated herein in their entirety.)

The invention relates to a method mediating protein-protein interactions comprising modulating the binding of a WW-domain containing polypeptide with a phosphorylated ligand. The ligand can be a protein, polypeptide, peptide, or peptide mimetic with a phosphoserine, phosphothreonine, or both a phosphoserine and phosphothreonine residue. The ligand can be a native ligand for the WW-domain containing polypeptide or a ligand mimic. A native ligand is meant to refer to a phosphorylated ligand which is known to bind a WW-domain. For example, Cdc25c is a native ligand for the WW-domain of Pin1. A phosphorylated ligand mimic can be a protein, polypeptide, peptide or peptide mimetic, that is a synthetic or natural organic product, which shares structural similarity with a native ligand for the WW-domain containing polypeptide and interacts with a WW-domain containing polypeptide and thus modulates the activity of the WW-domain containing polypeptide. Native ligands or ligand mimics that have a proline residue adjacent to a phosphorylated serine or threonine residue can bind the WW-domain. Proline residues in native ligands can be replaced with nonnative N-substituted residues to generate ligands mimics with enhanced binding affinity according to the procedure of Nguyan, J. T. et al., *Science* 282;207–211 (1998), the teachings of which are incorporated herein in their entirety.

The interaction between a WW-domain containing polypeptide and phosphorylated ligand can be modulated by increasing interactions (e.g., binding) between the WW-domain and phosphorylated ligand or inhibiting interactions (e.g., binding) between the WW-domain and phosphorylated ligand. For example, binding interactions between Pin1 and a subset of mitotic phosphoproteins can be competitively inhibited by a phosphorylated ligand mimic. For example, in the case of Pin1, the phosphorylated peptide Pintide is a ligand mimic which competes for binding of a native ligand to the WW-domain of Pin1 (See Example 4). Competitive inhibition is characterized by the ability of the phosphorylated ligand mimic to compete, alter or prevent the WW-domain containing polypeptide from interacting with its native ligand. Likewise binding interactions between the WW-domain of Pin1 and phosphorylated ligands can be enhanced by phosphorylation of specific amino acid residues in the WW-domain and target ligand.

The term "modulated" is used herein to describe biological activity greater (increased or enhanced or augmented activity) or less (decreased or reduced or diminished) than the activity of the WW-domain containing polypeptide in the absence of WW-domain/ligand interaction. As defined herein activity encompasses binding activity (e.g., ability to interact with a ligand) or enzymatic (e.g., ability to isomerize phosphoserine/threonine-proline bonds or ligase activity) activity or both. Enzymatic, catalytic or regulatory activity are used interchangeably. The enzymatic, catalytic or regulatory activity of the WW-domain containing polypeptide can control the activity of a ligand or the WW-domain containing polypeptide. For example, binding of the WW-domain of Pin1 to phosphoserine residues in synthetic peptides such as Pintide or mitotic cell extract proteins such as Cdc25, leads to an increase in the peptidyl propyl cis-trans isomerase activity (e.g., regulatory activity) of Pin1. The phosphoprotein or phosphopeptide specificity and affinity of WW-domain binding to ligands can be determined using binding and regulatory assays well known to those of skill in the art, and in vivo activity can be measured as described in Examples 1–10. For example, in vitro regulatory activity for Pin1 can be measured as described in Lu et al, U.S. Ser. No. 60/058,164 (1997), the teachings of which are incorporated herein by reference.

The activity of ligands described herein can be modulated following binding to WW-domains. Modulation of ligands can modulate protein-protein interactions resulting in, for example, the activation or deactivation of cell signaling pathways. Activation or deactivation of a cell signaling pathway can lead to the restoration of a biological function of the ligand. In particular, the WW-domain of Pin1 can interact with hyperphosphorylated tau and, thereby, allow Pin to restore microtubule function and assembly in neurodegenerative diseases. Tau protein is associated with several neurodegenerative diseases including Alzheimer's disease, Corticobasal degeneration, Dementia pugilistica, Down's syndrome, Frontotemporal dementias and Parkinsonism linked to chromosome 17, Myotonic dystrophy, Niemann-Pick disease, Parkinson-dementia complex of Guam, Pick's disease, postencephalic Parkinsonism, prion disease with tangles, progressive supranuclear palsy, subacute sclerosing panencephalistis. (Spillantini, M. G., et al., *TINS* 21:428–432(1998)). The methods of the present invention can be used to treat these neurodegenerative diseases. Specifically, in Alzheimer's disease, binding of the WW-domain of Pin1 to phosphorylated threonine 231 of tau can allow Pin1 to fully restore the function of phosphorylated tau (e.g., to bind microtubules and promote microtubule assembly) (Example 11). The WW-domain of Pin1 also binds phosphorylated threonine 668 of the amyloid precursor protein and can be used to treat neurodegenerative diseases associated with amyloid precursor protein. The WW-domain of WW-domain containing polypeptides can also interact (e.g., binds) with phosphoserine or phosphothreonine ligands thereby altering the conformation or activity of the WW-domain polypeptide. For example, the prolylpeptidyl cis-trans isomerase activity of the Pin1 is altered (e.g., increased) as a result of binding to a phosphorylated ligand such as Cdc25c. Thus, the activity of the WW-domain containing polypeptide can be altered (e.g., increased or decreased) after interaction (e.g., binding) with the phosphorylated ligand.

The invention further relates to methods of regulating cell growth by mediating the binding of the WW-domain of Pin1 to a mitotic regulatory protein such as NIMA or Cdc25. Binding can be mediated by regulating the phosphorylation state of a serine residue in the WW-domain of Pin1. In particular, the serine residue at position 16 of the WW-domain of Pin1 is dephosphorylated or phosphorylated resulting in cell growth and cell death, respectively. Cell growth (also referred to herein as cell proliferation) leads to an increase in the number of cells. Cell death can be programmed cell death such as apoptosis or the nonprogrammed cell death such as necrosis. Techniques to assess cell growth and cell death are well known to the skilled artisan.

The invention also relates to a method of regulating protein degradation comprising altering the phosphorylation state of a WW-domain target protein. In particular, the WW-domain containing polypeptide is Nedd4 and Nedd4 ligands are Cdc25C, amino acid permerases, the large subunit of RNA polymerase II and miloride-sensitive epithelial Na channel (ENaC), for example. When the ligand is phosphorylated, the WW-domain of Nedd4 binds the ligand and targets the ligand for protein degradation through a ubiquitin pathway. Dephosphorylation of the WW-domain prevents Nedd4 interaction with a ligand. Such a mechanism can be important in regulating mitotic activators such as Cdc25 thereby regulating cell growth. For example, modulating interactions between the WW-domain of Nedd4 and Cdc25 by preventing Nedd4 from targeting Cdc25 for protein degradation and results in cell death.

Also encompassed in the present invention are mutants of WW-domain containing polypeptides with altered binding or catalytic activity. The mutants of the present invention can be used, for example, to further understand the mechanism of protein-protein interactions which involve phosphoserine and phosphothreonine binding to WW-domains. The term "mutant", as used herein, refers to any modified nucleic acid sequence encoding a WW-domain or WW-domain containing polypeptide. For example, the mutant can be a polypeptide produced as a result of a point mutation or the addition, deletion, insertion and/or substitution of one or more nucleotides encoding the WW-domain, or any combination thereof. Modifications can be, for example, conserved or non-conserved, natural or unnatural. The invention also pertains to the nucleic acid constructs encoding the mutant WW-domain containing phosphoserine or phosphothreonine binding polypeptides and their encoded polypeptides. Techniques to introduce mutations are well established. Exemplary protocols are found in "Current Protocols in Molecular Biology", Ausbel, et al., John Wiley & Co. (1998).

As used herein a mutant also refers to the polypeptide encoded by the mutated nucleic acid. That is, the term "mutant" also refers to a polypeptide which is modified at one, or more, amino acid residues from the wildtype (naturally occurring) polypeptide. In a preferred embodiment mutants are generated by mutations in the WW-domain of polypeptides.

In one embodiment the mutations are made to Pin1. In another embodiment the mutations are made to Nedd4. In a particular embodiment, the amino-WW-domain of the Pin1, as described herein, has a mutation resulting in a altered binding or regulatory activity. For example, in this embodiment the Pin1$^{S16A}$ mutant is a mutant of Pin1 resulting from a point mutation substituting the serine at position 16 (S16) in the WW-domain of Pin1 with an alanine residue to generate the Pin1$^{S16A}$. In the wildtype Pin1 the proline ring of the ligand is positioned in a hydrophobic crevice between the aromatic rings of tyrosine 23 and tryptophan 34 of the WW-domain, whereas the phosphoserine residue of the ligand fits into a cleft between serine 16 and tyrosine 23 of the WW-domain (Macias, M. J., et al., Nature 382:646 (1996); Ranganathan, R., et al., Cell 89:875 (1997)). The phosphate moiety of the ligand is directed to within hydrogen binding distance of the tyrosine 23 hydroxyl proton.

A single alanine point mutation at tyrosine 23 (Pin1$^{Y23A}$) or tryptophan 34 (Pin1$^{W34A}$) in the WW-domain of Pin1 completely abolishes the ability of Pin1 to bind phosphopeptides with high affinity, whereas a single glutamic acid point mutation in the serine residue at position 16 (Pin1$^{S16E}$) abolishes the regulatory or isomerase activity of Pin1. Thus different amino acid residues in the WW-domain can mediate different activities (e.g., binding to ligands or enzymatic activity) of the WW-domain containing polypeptide.

WW-domain containing polypeptide mutants can be made by mutations to one, or more, amino acid residues selected from a group consisting of serine at position 16, or arginine at position 14, or tyrosine at position 23, or tryptophan at position 34 or any combination thereof.

Using well-known techniques to align amino acids, amino acid residues suitable for mutation as described herein for Pin-1 can be determined for other WW-domain containing polypeptides such as Nedd4, YAP, FE65, formin binding protein, dystrophin, utropin, Ess1p/Ptf1p, Rsp5, Pub1, Dodo, Msb1, ORF1, YKB2, DP71, C38D4.5, P9659.21, Yo61, Yfx1, ZK1248.15, KO15c11, CD45AP, FBP11, FBP21, FBP23, FBP28 and FBP30. (Rotin, D. Curr. Topics Microbiol. Immunol. 228:115 (1998)). Database accession numbers for the nucleotide and amino acid sequences for these WW-domain-containing proteins are known. (Rotin, D. Curr. Topics Microbiol. Immunol. 228:115 (1998)). Nucleic acid sequences encoding the WW-domain containing polypeptides can be mutated; the mutated nucleic acid constructs expressed under standard experimental conditions well known to the skilled artisan; and the resulting mutant polypeptides evaluated for binding or enzymatic activity or both as described herein. Appropriate amino acid residues can be substituted as described for Pin1 using routine, art-recognized techniques. (See, for example, Shen, M., et al., Genes & Dev 12:706 (1998)).

Techniques to assess ligand binding to a WW-domain-containing polypeptides are known in the art. Exemplary methods are described in Lu et al., U.S. Ser. No. 60/058,164 (1997), the teachings of which are incorporated herein by reference.

The WW-domain containing polypeptide is preferably purified substantially prior to use, particularly where the WW-domain or WW-domain containing polypeptide is employed in in vitro binding assays, in vivo treatments and in vitro screens of test substances which alter the activity of the WW-domain containing polypeptide or ligand. It is preferred to employ a WW-domain containing polypeptide which is essentially pure (e.g., about 99% by weight or to homogeneity).

WW-domain containing polypeptides can be screened for activity using standard techniques. To screen the WW-domain polypeptides for enzymatic activity, for example prolyl-peptidyl cis-trans isomerase activity, before and following binding and activation by ligands, in vitro assays with radiolabeled substrate in the presence or absence of phosphoserine or phosphothreonine peptides. The effects of WW-domain containing polypeptides and mutants can be assessed in vivo employing routine transformation techniques as described in Example 8.

The effect of WW-domain containing polypeptide interaction with a ligand on activity of the WW-domain containing polypeptide or the ligand can be tested. For example, particular biologic activities such as isomerase activity, ligase activity, cell proliferation, cell death or association with cellular targets such as neuronal microfilaments. Protocols to evaluate these biological activities are known to one of skill in the art. (See, for example, Lu et al., U.S. Ser. No. 60/058,164 (1997); Lu, K. P., et al., Nature 380:544 (1996), the teachings of which are incorporated herein by reference).

The present invention also provides methods of identifying a substance that modulates the interaction of WW-domain containing polypeptide and a phosphorylated ligand comprising the steps of contacting the WW-domain containing polypeptide with one, or more, test substances; maintaining the test substances and the WW-domain containing polypeptide under conditions suitable for interaction; and determining the interaction between the test substance and WW-domain containing polypeptide. An interaction between the test substance and the WW-domain containing polypeptide indicates that the test substance modulates the interaction between the WW-domain-containing polypeptide and the ligand. The interaction can be determined in the presence and absence of the test substance. One or more test substance can be evaluated simultaneously or sequentially. The test substances identified by the method of the invention can be used to treat disease conditions resulting from altered WW-domain containing polypeptide/ligand interactions.

The term "modulate" in regard to activity or "altered activity" or "altered interaction" is defined herein as activity different from that of the ligand or WW-domain in the absence of the test substance.

The test substance (e.g., an inhibitor or stimulator) can be added to the WW-domain polypeptide either before or following the addition of the ligand under conditions suitable for maintaining the WW-domain and ligand in a conformation appropriate for formation of a combination. Experimental conditions for evaluating test substances, such as buffer or media, concentration and temperature requirements, can, initially, be similar to those described in Examples 1–11. One of ordinary skill in the art can determine empirically how to vary experimental conditions depending upon the biochemical nature of the test substance. The concentration at which the test substance can be evaluated can be similar, more, or less than concentrations employed by the native ligand to bind the WW-domain containing polypeptide.

The substances which alter the activity of the WW-domain containing polypeptide or ligands of the invention can be stimulators/enhancers (e.g., agonists) or inhibitors (e.g., antagonists) of, for example, prolyl-peptidyl cis-trans isomerase or ubiquitin ligase activity. The substances can be polypeptides (including post-translationally modified polypeptides), peptides, or small molecules (including carbohydrates, steroids, lipids, other organic molecules, anions or cations).

The term "inhibitor", as used herein, refers to a substance which blocks, diminishes, antagonizes, hinders, limits, decreases, reduces, restricts or interferes with WW-domain containing polypeptide interaction with the ligand or WW-domain activity or ligand activity or any combination thereof, or alternatively and additionally, prevents or impedes the binding of the WW-domain polypeptide with a ligand thereby preventing the WW-domain or ligand from acting. By way of example, an inhibitor of Pin1 can decrease the ability of Pin1 to bind phosphorylated ligands or isomerize phosphoserine/phosphothreonine-proline bonds.

The term "stimulator" or enhancer as used herein, refers to a substance which agonizes, augments, enhances, increases, intensifies or strengthens the interaction between a WW-domain and ligand, or alternatively and additionally, mimics or enhances the effect of the binding of the WW-domain polypeptide to a ligand thereby further activating the WW-domain polypeptide or ligand. In the case of Pin1, a substance possessing stimulatory activity can increase peptidyl prolyl isomerase activity or can increase the binding affinity of Pin1 to phosphorylated ligands beyond that observed in the absence of the stimulatory substance. Likewise a stimulator of Nedd4 ligase activity can result in augmented targeting of polypeptides destined for protein degradation through ubiquitin pathways.

Inhibitors or stimulators/enhancers of WW-domain containing polypeptides or ligands of the present invention can include any molecule that binds or interferes with (inhibitor) or facilitates (stimulates) WW-domain interaction with its ligand or the activity or structure of the WW-domain or ligand. Encompassed by the present invention are inhibitor molecules that mimic the structure and conformation of the ligand or WW-domain. The inhibitors or stimulators of WW-domain containing polypeptides or ligands can be naturally occurring or synthesized using standard laboratory methods that are well known to those of skill in the art.

Another aspect of the invention relates to targeting a drug to treat a condition in a mammal by associating a drug with a WW-domain to form a "drug/WW-domain" complex and administering the "drug/WW-domain" complex to a mammal wherein the "drug/WW-domain" complex interacts with a phosphorylated ligand in vivo, thereby alleviating the condition. The condition to be treated results from an alteration in a phosphorylated ligand which is a ligand for a WW-domain containing polypeptide.

The invention further relates to modulating the interaction of a WW-domain and a phosphorylated ligand by designing a drug which interacts with a WW-domain. The drug, when administered to an individual, binds the WW-domain thereby modulating the interaction between the WW-domain and its phosphorylated ligand in vivo.

It is also envisioned that fragments of the WW-domain containing polypeptides can be used in the methods of the invention. "Fragments" of WW-domain containing polypeptides, as used herein, refer to any part of the WW-domain capable of binding to the phosphorylated ligand and mediating protein-protein interactions. For example, the isolated WW-domain of a WW-domain containing polypeptide would be considered a fragment.

In one embodiment of the present invention the WW-domains, WW-domain containing polypeptides, ligands or test substances are compounds comprising proteins, polypeptides and peptides. The proteins, polypeptides and peptides of the present invention comprise naturally-occurring amino acids (e.g., L-amino acids), non-naturally amino acids (e.g., D-amino acids), and small molecules that biologically and biochemically mimic the inhibitor or stimulation peptides, referred to herein as peptide analogs, derivatives or mimetics. (Saragovi, H. U., et al., *BioTechnology*, 10:773–778 (1992)). The protein, polypeptide or peptides of the present invention can be in linear or cyclic conformation.

The WW-domains, ligands or test substances of the present invention can be synthesized using standard laboratory methods that are well-known to those of skill in the art, including standard solid phase techniques. The molecules comprising polypeptides of naturally occurring amino acids can also be produced by recombinant DNA techniques known to those of skill, and subsequently phosphorylated or otherwise posttranslationally modified.

The WW-domains, ligands and test substances of the present invention can comprise either the 20 naturally occurring amino acids or other synthetic amino acids. Synthetic amino acids encompassed by the present invention include, for example, naphthylalanine, L-hydroxypropylglycine, L-3,4-dihydroxyphenylalanyl, α-amino acids such as L-α-hydroxylysyl and D-α-methylalanyl, L-α-methyl-alanyl, β amino-acids such as β-analine, and isoquinolyl.

D-amino acids and other non-naturally occurring synthetic amino acids can also be incorporated into the WW-domains, ligands or test substances of the present invention. Such other non-naturally occurring synthetic amino acids include those where the naturally occurring side chains of the 20 genetically encoded amino acids (or any L or D amino acid) are replaced with other side chains, for instance with groups such as alkyl, lower alkyl, cyclic 4-, 5-, 6-, to 7-membered alkyl, amide, amide lower alkyl, amide di(lower alkyl), lower alkoxy, hydroxy, carboxy and the lower ester derivatives thereof, and with 4-, 5-, 6-, to 7-membered heterocyclic.

As used herein, "lower alkyl" refers to straight and branched chain alkyl groups having from 1 to 6 carbon atoms, such as methyl, ethyl propyl, butyl and the like. "Lower alkoxy" encompasses straight and branched chain alkoxy groups having from 1 to 6 carbon atoms, such as methoxy, ethoxy and the like.

Cyclic groups can be saturated or unsaturated, and if unsaturated, can be aromatic or non-aromatic. Heterocyclic groups typically contain one or more nitrogen, oxygen, and/or sulphur heteroatoms, e.g., furazanyl, furyl, imidazolidinyl, imidazolyl, imidazolinyl, isothiazolyl, isoxazolyl, morpholinyl (e.g., morpholino), oxazolyl, piperazinyl (e.g., 1-piperazinyl), piperidyl (e.g., 1-piperidyl, piperidino), pyranyl, pyrazinyl, pyrazolidinyl, pyrazolinyl, pyrazolyl, pyridazinyl, pyridyl, pyrimidinyl, pyrrolidinyl (e.g., 1-pyrrolidinyl), pyrrolinyl, pyrrolyl, thiadiazolyl, thiazolyl, thienyl, thiomorpholinyl (e.g., thiomorpholino), and triazolyl. The heterocyclic groups can be substituted or unsubstituted. Where a group is substituted, the substituent can be alkyl, alkoxy, halogen, oxygen, or substituted or unsubstituted phenyl. (See U.S. Pat. Nos. 5,654,276 and 5,643,873, the teachings of which are herein incorporated by reference).

Biologically active derivatives or analogs of the above-described WW-domains, ligands and test substances (e.g., inhibitors or stimulators), referred to herein as peptide mimetics, can be designed and produced by techniques known to those of skill in the art. (See e.g., U.S. Pat. Nos. 4,612,132; 5,643,873 and 5,654,276, the teachings of which are herein incorporated by reference). These mimetics can be based, for example, on a specific WW-domain sequences or known ligands and maintain the relative positions in space of the WW-domain or ligand. These peptide mimetics possess biologically activity (e.g., prolyl-peptidyl cis-trans isomerase, ubiquitin ligase or microtubule binding activity) similar to the biological activity of the corresponding WW-domain containing polypeptide ligand or test substance, but possess a "biological advantage" over the corresponding peptide with respect to one, or more, of the following properties: solubility, stability, and susceptibility to hydrolysis and proteolysis.

Methods for preparing peptide mimetics include modifying the N-terminal amino group, the C-terminal carboxyl group, and/or changing one or more of the amino linkages in the peptide to a non-amino linkage. Two or more such modifications can be coupled in one peptide mimetic inhibitor. Modifications of peptides to produce peptide mimetics are described in U.S. Pat. Nos: 5,643,873 and 5,654,276, the teachings of which are incorporated herein by reference.

Where the WW-domains, ligands or test substances of present invention comprise amino acids, the peptides can also be cyclic proteins, peptides and cyclic peptide mimetics. Such cyclic peptides can be produced using known laboratory techniques (e.g., as described in U.S. Pat. No: 5,654,276, the teachings of which are herein incorporated in their entirety by reference).

The test substances identified as inhibitors or stimulators as described herein can be used in vitro to study cell cycle regulation, mitotic events, protein degradation and neurodegenerative diseases. For example, the WW-domain of the present invention can be used to evaluate mitotic events and programmed cell death in mammalian cells by interacting with specific phosphoproteins and evaluating the effects on the cell cycle and apoptosis. By way of illustration, the WW-domain of Pin1 can bind phosphorylated tau protein or amyloid precursor protein and restore neuronal function or promote neuronal survival in Alzheimer's disease by preventing cell death (e.g., apoptosis).

The present invention provides methods of modulating the activity of WW-domain containing polypeptides or their ligands comprising modulating the interaction of the WW-domain with a ligand, wherein the ligand contains a phosphoserine or phosphothreonine. Ligands refer to any molecule (e.g., polypeptide, peptide mimetic, or small organic molecule) which interacts with a WW-domain or WW-domain containing polypeptide. Methods to detect binding can include, for example, the use of labeled (e.g., fluorescent, biotin, radioactive, luminescent) activated WW-domains or ligands and detection techniques such as solid-phase plate assays; immunoprecipitation; Western blotting, and fluorescence aniostropy assays. Such technologies are well established and within the technical expertise of one of ordinary skill in the art.

The identification of substances which alter (e.g., inhibit or stimulate) WW-domain ligand interaction as identified herein can be important in defining pathways which lead to carcinogenesis and to the development of novel, specific and more effective treatment regimens.

Certain WW-domain containing polypeptide play a key role in transducing signaling pathways to mediate, for example, cell division and apoptosis (e.g., Pin1), and protein degradation (e.g., Nedd4). It is further envisioned that the WW-domains and mutants of the present invention and substances which alter their activity can be used to evaluate, interfere and treat events such as cell spreading in metastatic cancers.

As another example, because Pin1 is critical regulator for mitosis (Lu, K. P., et al., U.S. Ser. No. 60/058,164 (1997); Shen, M., et al., *Genes & Development* 12:706–720 (1998)) and substances which alter (e.g., inhibit) the activity of a WW-domain can be used to discern the mechanisms for certain aspects of cell division such as embryonic development. The identification of substrates for and substances which alter WW-domain containing polypeptides and their ligands can be useful for the study of cell cycle events.

The inhibitors or stimulators of interactions between WW-domain and ligands of the present invention can be used to interfere with eukaryotic cell growth and to treat hyperplastic and neoplastic disorders in mammals. As defined herein, mammals include rodents (such as rats, mice or guinea pigs), domesticated animals (such as dogs or cats), ruminant animals (such as horses, cows) and primates (such as monkeys or humans). For example, a phosphorylation of the WW-domain of Pin1, which attenuates some cell signaling pathways, can be useful in anti-neoplastic therapies for the treatment of diseases such as leukemia. Certain neoplasms have been attributed to an augmentation in the phosphorylation of cellular effectors which can be offset or neutralized by wildtype or mutant of WW-domains thereby turning off or controlling the unregulated cellular growth or pathway.

Neoplastic and hyperplastic disorders include all forms of malignancies, psoriasis, retinosis, atherosclerosis resulting from plaque formation, leukemias and benign tumor growth. For example, such disorders include lymphomas, papilomas, pulmonary fibrosis, and rheumatoid arthritis.

The methods of the present invention can be used to modulate protein-protein interactions in neurodegenerative diseases to restore neuronal function or prevent neuronal cell death, and alleviate disease symptoms. Neurodegenerative diseases that can be treated by the methods of the present invention include Alzheimer's disease, multiple sclerosis, muscular dystrophy Corticobasal degeneration, Dementia pugilistica, Down's syndrome, Frontotemporal dementias and Parkinsonism linked to chromosome 17, Myotonic dystrophy, Niemann-Pick disease, Parkinson-dementia complex of Guam, Pick's disease, postencephalic Parkinsonism, prion disease with tangles, progressive supranuclear palsy, subacute sclerosing panencephalistis. (Spillantini, M. G., et al., *TINS* 21:428–432 (1998)). As an example, the WW-domain of Pin1 can bind phosphorylated tau protein or amyloid precursor protein and restore nerve cell function, prevent apoptosis, or both.

Biologically active derivatives, analogs or mimics of the above-described WW-domains, ligands, test substances, drug/WW-domain complexes and drugs designed to interact with a WW-domain can be formulated into compositions with an effective amount of the WW-domain, ligand, drug/ WW-domain complex, or drug as the active ingredient. Such compositions can also comprise a pharmaceutically acceptable carrier, and are referred to herein as pharmaceutical compositions. The inhibitor or stimulation compositions of the present invention can be administered intravenously, parenterally, orally, nasally, by inhalation, by implant, by injection, or by suppository. The mode of administration is preferably at the location of the target cells. The inhibitor or stimulation composition can be administered in a single dose or in more than one dose over a period of time to achieve a level of inhibitor which is sufficient to confer the desired effect.

Suitable pharmaceutical carriers include, but are not limited to sterile water, salt solutions (such as Ringer's solution), alcohols, polyethylene glycols, gelatin, carbohydrates such as lactose, amylose or starch, magnesium stearate, talc, silicic acid, viscous paraffin, fatty acid esters, hydroxymethylcellulose, polyvinyl pyrolidone, etc. The pharmaceutical preparations can be sterilized and desired, mixed with auxiliary agents, e.g., lubricants, preservatives, stabilizers, wetting agents, emulsiers, salts for influencing osmotic pressure, buffers, coloring, and/or aromatic substances and the like which do not deleteriously react with the active compounds. They can also be combined where desired with other active substances, e.g., enzyme inhibitors, to reduce metabolic degradation.

For parenteral application, particularly suitable are injectable, sterile solutions, preferably oily or aqueous solutions, as well as suspensions, emulsions, or implants, including suppositories. Ampules are convenient unit dosages.

It will be appreciated that the actual effective amounts of an inhibitor or stimulation in a specific case can vary according to the specific inhibitor compound being utilized, the particular composition formulated, the mode of administration and the age, weight and condition of the patient, for example. As used herein, an effective amount of inhibitor is an amount of inhibitor which is capable of inhibiting the phosphatase activity of the phosphatase of interest, thereby inhibiting target cell growth and resulting in target cell death, for example. Dosages for a particular patient can be determined by one of ordinary skill in the art using conventional considerations, (e.g. by means of an appropriate, conventional pharmacological protocol).

The present invention further relates to a method of treating a WW-domain containing polypeptide-mediated condition in a mammal, wherein the condition results from alteration in the WW-domain or WW-domain ligand, comprising introducing into the mammal an amount of substance effective to regulate the WW-domain or ligand activity in the mammal, thereby alleviating the condition. Regulation of WW-domain or ligand activity can be up-regulation (e.g., an increase or enhancement in ligase or PPIase activity) or down-regulation (e.g., a decrease or inhibition in ligase or PPIase).

The WW-domains, WW-domain-containing protein (e.g., Pin1, Nedd4), mutants, or drugs of the present invention can be used to treat a WW-domain-mediated condition or disease in a mammal wherein the condition results from an alteration in the regulation of WW-domain or its ligand activity, comprising delivering to target cells the WW-domain or mutant described herein, or a nucleic acid sequence encoding the activated phosphatase, in vitro or in vivo, wherein the amount of the WW-domain or mutant introduced effectively alters the interaction between a WW-domain and its ligand in a target cell in a mammal. The phrase "WW-domain polypeptide-mediated disease or condition" is intended to refer to a cellular process wherein the endogenous activity of the WW-domain or its ligand is not sufficiently regulated, for example, as a result of inadequate cellular levels or activity of a WW-domain or alternatively and additionally, a condition wherein the levels or activity of a WW-domain ligand exceeds the capacity of the endogenous WW-domain thereby resulting in a cell in which the delicate balance of activity is disturbed. For example, a WW-domain of Pin1, Pin1 protein, Pin1 mimic, WW-domain, or WW-domain mimic can be used to regulate a condition arising from hyperphosphorylation or a protein such as tau in Alzheimer's disease. Thus, the WW domains of the invention can be used experimentally or therapeutically to reduce or enhance the activity of ligands. WW-domain polypeptide mediated diseases or conditions can be, for example, uncontrolled cell growth or proliferation such as neoplastic disorders or cell death.

The WW-domain of the invention can be delivered to a cell by the use of vectors comprising one or more nucleic acid sequences encoding the WW-domain. Vectors, as used herein, can include viral and non-viral vectors. Examples of nonviral vectors are lipids or liposomes (U.S. Pat. No. 5,676,954, the teachings of which are incorporated herein by reference). Alternatively, DNA can be introduced into cells via a gene gun, as described in (Tynan, E. F., et al., *Proc. Natl. Acad. Sci. USA.*, 90:11478–11482 (1993)). The nucleic acid sequence can be been incorporated into the genome of the viral vector. In vitro, the viral vector containing the WW-domain described herein or nucleic acid sequences encoding the WW-domain can be contacted with a cell and infectivity can occur. The cell can then be used experimentally to study, for example, unrestricted cell growth in vitro or be implanted into a patient for therapeutic use. The cell can be migratory, such as hematopoietic cells, or non-migratory such as a solid tumor or fibroblast. The cell can be present in a biological sample obtained from the patient (e.g., blood, bone marrow) and used in the treatment of disease such as Alzheimer's or muscular dystrophy, or can be obtained from cell culture and used to dissect cell proliferation, cell death or protein degradation pathways in in vivo and in vitro systems. After contact with the viral vector comprising the WW-domain or a nucleic acid sequence encoding the WW-domain, the sample can be returned or readministered to a cell or patient according to methods known to those practiced in the art. In the case of delivery to a patient or experimental animal model (e.g., rat, mouse, monkey, chimpanzee), such a treatment procedure is sometimes referred to as ex vivo treatment or therapy. Frequently the cell is targeted from the patient or animal and returned to the patient or animal once contacted with the viral vector comprising the activated mutant of the present invention. Ex vivo gene therapy has been described, for example, in Kasid, et al., *Proc. Natl. Acad. Sci. USA* 87:473 (1990); Rosenberg, et al., *New Engl. J. Med.* 323:570 (1990); Williams, et al., *Nature* 310476 (1984); Dick, et al., *Cell* 42:71 (1985); Keller, et al., *Nature* 318:149 (1985) and Anderson, et al., U.S. Pat. No. 5,399,346 (1994).

Where a cell is contacted in vitro, the cell incorporating the viral vector comprising a nucleic acid sequence of the WW-domain can be implanted into a patient or experimental animal model for delivery or used in in vitro experimentation to study cellular events mediated by WW-domain containing polypeptides such as certain aspects of cell growth, cell death, protein processing, and neuronal regulation.

Where the viral vector comprising the WW-domain phosphatase of the invention or an isolated nucleic acid sequence encoding the WW-domain is delivered to a patient or experimental animal, the mode of administration is preferably at the location of the cells which are to be treated. As such, the administration can be nasally (e.g., as in administering a vector expressing ADA), orally (e.g., as in an inhalant or spray as in administering a vector expressing the cystic fibrosis transmembrane conductance regulator (CFTR)) or by injection (e.g., as in administering a vector expressing a suicide gene to a tumor). Other modes of administration (e.g., parenteral, mucosal, systemic, implant or intraperitoneal) are generally known in the art. The substances can, preferably, be administered in a pharmaceutically acceptable carrier, such as saline, sterile water, Ringer's solution, and isotonic sodium chloride solution.

Generally, viral vectors which can be used therapeutically and experimentally are known in the art. Examples include the vectors described by Srivastava, A., U.S. Pat. No. 5,252,479 (1993); Anderson, W. F., et al., U.S. Pat. No. 5,399,346 (1994); Ausubel et al., "Current Protocols in Molecular Biology", John Wiley & Sons, Inc. (1998). Suitable viral vectors for the delivery of nucleic acids to cells include, for example, replication defective retrovirus, adenovirus, parvovirus (e.g., adeno-associated viruses), and coronavirus. Examples of retroviruses include avian leukosis-sarcoma, mammalian C-type, B-type viruses, lentiviruses (Coffin, J. M., "Retroviridae: The Viruses and Their Replication", In: *Fundamental Virology*, Third Edition, B. N. Fields, et al., eds., Lippincott-Raven Publishers, Philadelphia, Pa., (1996)). Viral vectors infect cells by known mechanisms thereby delivery the activated mutant protein tyrosine phosphatase or the nucleic acid encoding the activated phosphatase. The mechanism of infectivity depends upon the viral vector and target cell. For example, adenoviral infectivity of HeLa cells occurs by binding to a viral surface receptor, followed by receptor-mediated endocytosis and extrachromosomally replication (Horwitz, M. S., "Adenoviruses" In: *Fundamental Virology*, Third Edition, B. N. Fields, et al., eds., Lippincott-Raven Publishers, Philadelphia, Pa., (1996)).

The present invention describes a novel function of the WW-domain as a phosphoserine or phosphothreonine binding module. For example, the WW-domain mediates phosphorylation-dependent interactions between Pin1 and a defined subset of mitosis-specific proteins, and neuronal proteins such as tau and amyloid precursor protein. These interactions are essential for the Pin1 mitotic function in the cell and are highly regulated by phosphorylation of Pin1. Thus, the WW-domain plays a crucial role in regulating the function of the essential mitotic PPIase Pin1.

Serine phosphorylation, often on PSET sequences (rich in Pro, Glu, Ser and Thr), controls the timing of ubiquitination of a variety of proteins, and ubiquitin-protein ligases are responsible for substrate recognition (Rechsteiner, M. et al., *TIBS* 21:267–271 (1996); Clurman, B. E. et al., *Genes Dev* 10:1979–1990 (1996); Won, K. A. et al., *EMBO J* 16:3797–3804 (1997); Verma, I. M., et al., *Proc Natl Acad Sci USA* 94:11758–11760 (1997)). The ligase Nedd4 has been shown to ubiquitinate protein substrates in a phosphorylation-dependent manner. For example, ubiquitination of uracil permease by the budding yeast Nedd4 homologue RSP 5 depends on phosphorylation on a PEST sequence and ubiquitination of Cdc25 by the fission yeast homologue Pub1 occurs in mitotic cells, where Cdc25 is heavily phosphorylated (Hein, C. et al., *Mol. Micro* 18:77–87(1995); Galan, J. et al., *EMBO J* 16:5847–5854 (1997); Marchal, C. et al. *Mol Cell Biol* 18:314–321 (1998); Nefsky, B. et al., *EMBO J* 15:1301 (1996)).

The present invention shows that the phosphorylated form of Cdc25 can specifically interact with Nedd4 WW-domains. These results document a novel ubiquitination mechanism, where WW-domains of a ubiquitin ligase bind pSer-containing sequences, targeting catalytic domain of the ligase to phosphorylated substrates to initiate protein degradation. This mechanism can be used to degrade Cdc25C at the late stage of mitosis (Hein, C. et al, *Mol. Micro* 18:77–87(1995); Galan, J. et al., *EMBO J* 16:5847–5854 (1997); Marchal, C. et al. *Mol Cell Biol* 18:314–321 (1998); Nefsky, B. et al., *EMBO J* 15:1301 (1996)). Three mammalian Nedd4-like genes have been identified, each containing four WW-domains (Rotin, D. *Curr. Top. Microbiol. Immunol* 228:115 (1998); Pirezzi, G. et al., *J. Biol. Chem.* 272:14611 (1997)). Although the affinity of Nedd4 WW-domains for pSer sequences is not as high as that of Pin1 WW-domain, multiple WW-domains can increase the affinity of ligases for phosphorylated substrates and/or allow enzymes to interact with a range of the substrates.

Both NMR and X-ray structural analysis show that the overall structures of WW-domains are almost identical whether the WW-domain is expressed as an isolated domain or present in its native polypeptide (Macias, M. J. et al., *Nature* 382:646 (1996); Ranganathan, K. et al., *Cell* 89:875 (1997)), indicating that the WW-domain-binding sequences have been identified, namely PPLP and PPXY motifs (Rotin, D. *Curr. Top. Microbiol. Immunol* 228:115 (1998); Bedford, M. T. et al., *EMBO J* 16:2376 (1997)).

The present invention shows the WW-domain is a tightly regulated novel pSer binding module. The amino acids Tyr-23 and Trp-34 in the WW-domain of Pin1 are critical for phosphoserine or phosphothreonine binding, and Ser-16 is important for regulation of catalytic activity. Tryptophan residues are frequently used to mediate the interactions with the phosphate group of pSer (Copley, R. R. et al., *J. Mol. Biol.* 242:321 (1994)). For example, in the NMR structure of the pKID/KIX complex, the interactions are stabilized by hydrogen bonding interactions between the phosphate moiety of pSer in pKID and the hydroxyl group of a Tyr residue in KIX (Radharkrishman, I. et al., *Cell* 91:741 (1997)). Furthermore, the present invention shows that here for the WW-domain binding of Pin1 to a ligand, and Ala substitution of the analogical Tyr, but not Lys, disrupts the interactions between pKID and KIX, despite the proximity of Lys to pSer. Thus, it is likely that the interactions between the Pin1 WW-domain and phosphoproteins are stabilized by the hydrogen bonding interactions between the hydroxyl group of Tyr-23 and the phosphate moiety of pSer and that these interactions are disrupted upon phosphorylation of Ser-16 because of the negatively charged phosphate group and hydrogen bonding interactions with the Tyr-23 side chain.

The three amino acid residues critical for binding and regulation of the Pin1 WW-domain (Ser 16; Tyr 23, Tyr 24) are found in a subset of other WW-domains, including one in dystrophin (Rotin, D., *Curr. Top. Microbiol. Immunol.* 228:115 (1998)). Dystrophin is a protein product of the gene responsible for Duchenne and Becker muscular dystrophy. Similar to Pin1, dystrophin is also associated with a group of membrane proteins (Bonneman, C. G. et al, *Curr. Opin. Pediatr.* 8:569); Winder, S. J., *J. Muscle Res. Cell. Motil* 18:617 (1997)). Phosphorylation is suggested to regulate the formation of the dystrophin complexes (Luise, M. et al., *Biochem J.* 293:243 (1993); Shemanko, C. S. et al. *Mol. Cell. Biobhem* 152:63 (1995)).

PPIases catalyze rotation about the peptide bond preceding a Pro residue, thereby regulating the confirmation of substrates (Dolinski, K. et al., *Proc. Natl Acad sci: USA* 94:13093 (1997)). Pin1 is a unique PPIase that is required for isomerization of the phosphorylated Ser/The-Pro peptide bond and regulated activity of phosphoproteins (Schutkowski, M. et al. *Biochemistry* 37:5566 (1998); Shen, M. et al. *Genes & Development* 12:706 (1998)). PPIase-negative mutants reduce the affinity of Pin1 for phosphoproteins, suggesting that PPIase activity can affect phosphoprotein binding. The present invention shows that the PPIase domain alone can bind the phosphopeptide and also display the pSer/The-Pro-specific PPIase in vitro. However, the PPIase domain has about 10 fold lower affinity for the phosphopeptide than the WW-domain, and, the PPIase domain alone can not interact with protein substrates in vitro, or carry out the Pin1 function in vivo. These results indicate that an additional targeting function is required to confer the specificity of the PPIase domain. Interestingly, the WW-domain displays a much higher affinity for the phosphopeptide and directly interacts with mitotic phosphoproteins. Furthermore, WW-domain point mutations that disrupt its ability to bind phosphoproteins abolish the Pin1 function in the cell. These results indicate that, by interacting with pSer-Pro motifs, the WW-domain functions as a targeting domain, allowing the efficacious interaction between the enzyme and substrates.

A common feature of Pin1-binding proteins (MPM-2 antigens) is phosphorylated on multiple Ser/Thr residues clustered at the regulatory domain of molecules during mitosis (Izumi, T. et al., *Mol. Biol. Cell* 6:215 (1995); Kumagai, A. et al., *Science* 273:1377 (1996); Ye, X. S. et al., *EMBO J* 14:986 (1995)). Phosphorylation on multiple sites is necessary for activity, or to mutate multiple phosphorylation sites to disrupt the functions. For example, multiple phosphorylation events in Cdc25C and NIMA, whose functions are regulated by Pin1, are important for their mitotic function (Izumi, T. et al., *Mol. Biol. Cell* 6:215 (1995); Kumagai, A. et al., *Science* 273:1377 (1996);; Ye, X. S. et al., *EMBO J* 14:986 (1995)). These results suggest that multiple phosphorylation events are required for regulating the function of Pin1 target proteins. Little is known how to coordinate these multiply phosphorylated events into "all-or-nothing" activity.

SH2 domains have been demonstrated to be critical for generating processive phosphorylation by nonreceptor tyrosine kinases (Songyang, Z. et al. *Nature* 373:536 (1995); Mayer, B. J. et al., *Curr. Biol.* 5:296 (1995)). SH2 domains in these kinases prefer to bind phosphotyrosine residues that have been phosphorylated by its own catalytic domain. The resulting high phosphorylation of substrates on multiple sites (Songyang, Z. et al. *Nature* 373:536(1995); Mayer, B. J. et al., *Curr. Biol.* 5:296 (1995)). WW-domains can facilitate the processive isomerization of proteins that have been phosphorylated by mitotic kinases at multiple sites. The processive isomerization is triggered by binding of the higher affinity WW-domain of Pin1 to a Ser-phosphorylated site on a substrate protein. Once bound, the high local concentration drives isomerization of all sites that are sterically accessible to the lower affinity catalytic PPIase domain. This can provide a means by which to generate coordinate "all-or-nothing" activity of mitotic phosphoproteins and subsequently sequential mitotic events.

The following Examples are offered for the purpose of illustrating the present invention and are not to be construed to limit the scope of this invention. The teachings of all references cited herein are hereby incorporated by reference.

EXAMPLE 1

WW-Domains Interact with Phosphorylated Ligands

Pin1 WW-Domains

GST-fusion proteins containing the WW-domain, PPIase-domain or the entire Pin 1 protein were prepared and incubated with interphase (G1/S arrested; Control) or dividing (M phase) HeLa cell extracts using well-known procedures (Lu, K. P., et al., *Nature* 380:544 (1996); (Shen, M., et al., *Genes & Devl.* 12:706 (1998)). Briefly, HeLa cells were arrested at the G1/S boundary or mitosis by incubation with thymidine and aphidicolin or nocodazole for 16 h, respectively. The cells were lysed and supernatants incubated with 10 $\mu$l of agarose beads containing GST-Pin1; GST-WW-domain of Pin1; GST-PPIase domain of Pin1; or control GST for 2 h at 4° C. The phosphorylated precipitated proteins were washed 5 times in buffer containing 1% Triton X-100 before subjecting to immunoblotting analysis using MPM-2 antibody, as described previously (Yaffe, M. B. et al., *Science* 278:1957 (1997); Schukowski, et al., *Biochemistry* 37:5566 (1998); Shen, M. et al., *Genes & Dev* 12:706 (1998)). MPM-2 recognizes a subset of mitotic phosphoproteins including Pin1-binding proteins such as cdc25.

Intense signal, indicative of strong binding, was detected in extracts from mitotic HeLa cell extracts incubated with the entire Pin1 protein or its WW-domain, but not when mitotic extracts were incubated with the PPIase domain. These data show that the WW-domain of Pin1 is responsible for Pin1 binding to phosphorylated ligands. No specific binding was observed in interphase extracts incubated with WW-domain PPIase domain or the entire Pin1 protein. Similar results were also obtained with the isolated WW-domain from Ess1/Ptf1, the yeast Pin1 homologue. In contrast, no specific binding was observed for the isolated PPIase domain of Pin1 or when control GST was incubated with either interphase or mitotic HeLa cell extracts. These results show that the WW-domain not the catalytic PPIase domain, is responsible for phosphoprotein binding of Pin1, a property which is highly conserved in humans (Pin 1) and yeast (Ess1/Ptf1).

NEDD4 WW-domains

NEDD4 and its yeast homologues Rsp5 and Pub1 are ubiquitin protein ligases containing three or four WW-domains (Rotin, D. *Curr. Top. Microbiol.* 228:115–133 (1998)). The Nedd4 yeast homologues ubiquitinate the phosphoproteins uracil permease and Cdc25C (Hein, C., et al., *Mol. Micro.* 18:77–87 (1995)), which do not contain the typical Pro-rich motif (Rotin, D., *Curr. Top. Microbiol. Immunol.* 228:115–133 (1998)). In contrast to the Pin1 WW-domain, the Nedd4 WW-domain-2 bound only a few MPM-2 antigens in GST pulldown experiments with HeLa cell extracts. To detect interactions with other phosphoproteins, Nedd4 WW-domain-1 and -2 were used to bind $^{32}$P or $^{35}$S-labeled cell lysates. HeLa cells were labeled overnight with $^{32}$P orthophosphate or $^{35}$S-Met, as described (Lu, K. P., et al, *J. Biol. Chem.* 268:8769 (1993)). Cells were lysed in lysis buffered with or without phosphatase inhibitors (40 mM glycerol phosphate, 50 mM NaF, 10 mM Na VO4 and 2 $\mu$M okadeic acid) (Shen, M., et al., *Genes & Dev.* 12:706 (1998)). For dephosphorylation experiments, three Ser phosphatases (CIP, PP1 and PP2A) were added to lysates for 30 min at 30° C. in the absence of presence of the phosphatase inhibitors, as described previously (Lu, K. P., et al., *J. Biol. Chem.* 268:8769 (1993)).

Control GST bound only few minor labeled proteins, whereas both Nedd4 WW-domains bound a similar subset of proteins from labeled lysates. When cell lysates were pretreated with Ser phosphatases, the ability of the WW-domains to bind most cellular proteins was reduced by approximately 10 fold. Binding was restored to approximately half of that observed with controls when phosphatase inhibitors were included. Similar results were also obtained between Pin1 or dystrophin WW-domain but with different subsets of phosphoproteins. These results indicate that different WW-domains interact with distinct subsets of phosphoproteins in a phosphorylation-dependent manner.

To confirm that Nedd4 WW-domains bind a specific phosphoprotein in a phosphorylation-dependent manner interactions between Nedd4 WW-domains and Cdc25C were examined. To various degrees, all three Nedd4 WW-domains bound the mitotically phosphorylated form, but not the interphase phosphorylated form of both HeLa Cdc25C and in vitro synthesized Xenopus Cdc25C. Peptide binding assays showed that the Nedd4 WW-domain-2 also exhibited a significant phosphorylation-dependent affinity towards both Pintide and the Cdc25C peptide (Table 1). The Kd values for the phosphopeptides were also lower than those for the Pro-rich peptide that was thought to be a Nedd4 WW-domain-binding site (Table 1) (Chen, H. I., et al., *Proc. Natl. Acad. Sci. USA* 92:7819 (1995); Staub, O., et al., *EMBO J.* 15:2371 (1996); Bedford, M. J., et al., *EMBO J.*, 16:2376 (1997)). These results demonstrate that, like the Pin1 WW-domain, Nedd4 WW-domains also bind pSer-containing sequences.

TABLE 1

Binding constants of WW-domains and peptides

|  | Pintide | | Cdc25 Peptide | | Pro-Rich |
| --- | --- | --- | --- | --- | --- |
| WW-domain | WFYp-SPFLE Kd ($\mu$M) | WFY-SPFLE Kd ($\mu$M) | EQPLp-TPVTDL Kd ($\mu$M) | EQPL-TPVTDL Kd ($\mu$M) | IPGTP-PPNYD Kd ($\mu$M) |
| Pin1 WW-domain | 1.0 | N.B. | 2.2 | N.B.* | N.B. |
| Nedd4 WW-domain | 10.0 | N.B. | 20.0 | N.B.* | >40† (47–118+‡) |

The N-terminus of peptides was labeled with fluorescein and purified by TLC. Different concentrations of GST-WW-domains and control GST were incubated with the labeled peptides (WFYpSPFLE, SEQ ID NO: 8; WFYSPFLE, SEQ ID NO: 9; EQPLpTPVTDL, SEQ D NO: 10; EQPLTPVTDL, SEQ D NO: 11; and IPGTPPPNYD, SEQ D NO: 12) and dissociation constants were measured by fluorescence aniostropy assay. Each value represents the average of three independent experiments. No binding was detected between GST and all peptides used.
N.B., not binding detected;
*, not binding detected by incubating the GST-WW-domain with the peptide immortalized on a membrane, followed by immunoblotting analysis using GST antibody;
†, an estimated Kd since binding did not reach the plateau even when the WW-domain was used at 100 $\mu$M, the highly concentration that could be used in this assay;
‡, previously reported Kds for the interaction between the Yap WW-domain and various Pro-Rich peptides (Macias, M.J., et al., Nature 382:64 Ranganathan, K.P., et al., Cell 89:875 (1997)).

EXAMPLE 2

WW-domain Binding Depends upon Phosphorylation of Ligands and Protects the Ligand from Dephosphorylation Interactions between the WW-domain of Pin1 and specific phosphorylated ligands were examined. To detect phosphorylation-dependent interaction, Cdc25C, Plk1 and Pin1 ligands, were synthesized by in vitro transcription and translation in the presence of $^{35}$S-Met and incubated with Xenopus interphase or mitotic extracts or mitotic extracts followed by treatment with calf intestine phosphatase (M+CIP). Protein complexes were separated on SDS-gels either directly (input) or first subjected to GST pull down with the N-terminal WW-domain (amino acids 1–54) or C-terminal PPIase domain (amino acids 47–163) or the entire Pin1 protein (Shen, M. et al., *Genes & Dev* 12:706 (1998)). The labeled protein-GST bead complexes were washed extensively and bound proteins analyzed by SDS-PAGE and autoradiography using standard techniques.

To determine whether WW-domain binding protects dephosphorylation of its targets $^{35}$S labeled (His)$_6$ epitope tagged Cdc25C was phosphorylated by mitotic extracts and precipitated by GST fusion protein beads or Ni-NTA beads. The isolated Cdc25C was then incubated with control buffer or CIP, followed by separation on SDS-containing gels and autoradiography.

The isolated WW-domain of Pin1 and Pin1 bound the phosphorylated Cdc25C in mitotic cell extracts, but not interphase extracts. The WW-domain did not bind Cdc25C when the mitotically phosphorylated Cdc25C was dephosphorylated by calf intestine phosphatase (CIP) prior to the binding. When mitotically phosphorylated Cdc25C was precipitated using GST beads containing Pin1 or its WW-domain, CIP failed to dephosphorylate Cdc25C. In contrast, CIP was able to dephosphorylate Cdc25C almost completely when precipitated by Ni-NTA beads against the N-terminal His tag. Similar results were obtained with another Pin1-binding protein Plk1. These results demonstrate that WW-domain binding depends on phosphorylation of target proteins and when bound to a protein ligand the WW-domain protects the target protein from dephosphorylation.

EXAMPLE 3

Identification of Pin1 WW-domain Binding Sites in Cdc25C by Peptide Scan

Arrays of thirteen amino acids with ten amino acid overlaps corresponding to protein sequences in Cdc25C were synthesized and their C-termini linked through a β-Ala residue and decaethyleneglycol to a cellulose matrix (Rudiger et al., (*EMBO J.*, 16:1501 (1997)). A total of 270 thirteen amino acid peptide sequences were analyzed.

Positions 1–155 represent a complete peptide scan of human Cdc25C with all conserved Ser/Thr-Pro motifs in phosphorylated form, whereas positions 156–270 represent nonphosphorylated peptide scan, which covers regions of Cdc25C that contain Ser/Thr-Pro motifs. The peptide bond cellulose membranes were incubated with Pin1 or GST-Pin1 WW-domain, and washed, followed by immunoblotting using anti-Pin1 antibodies or anti-GST antibodies, as described Rudiger et al., (*EMBO J.*, 16:1501 (1997)). Similar results were obtained with either Pin1 or Pin1 WW-domain. High affinity Pin1 WW-domain-binding sites were located at Thr48 and Thr67 in Cdc25C.

EXAMPLE 4

WW-Domain Binding to the Ligand is Inhibited by Phosphorylated Peptides

To examine the ability of a phosphopeptide to compete with phosphoproteins for binding to the WW-domain, the Pin1 binding phosphopeptide Pintide (WFYpSPRLKK, SEQ ID NO: 13) (Lu, K. P. et al., U.S. Ser. No. 60/058,164 (1997)) was used in competition assays. A nonphosphorylated counterpart of Pintide (WFYSPRLKK, SEQ ID NO: 14) (C-Pintide) was used as a control.

Figure 1:
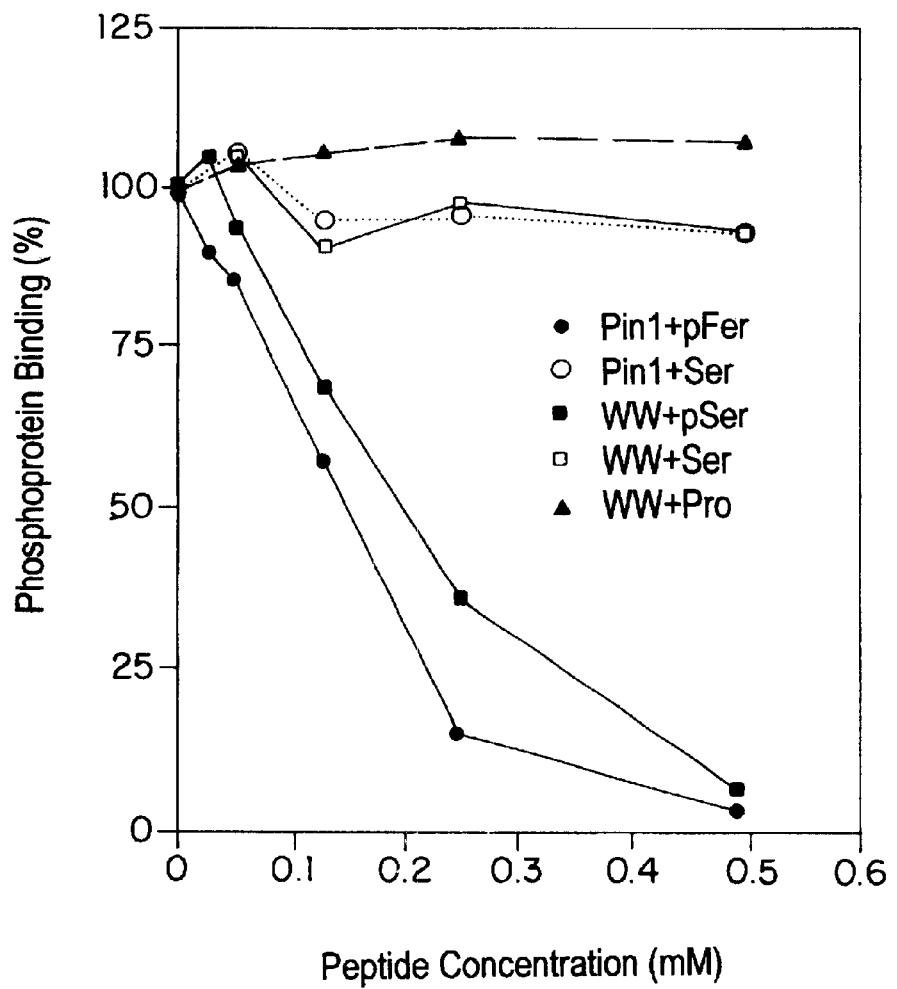
FIG. 1 is a graphic representation of the competition of Pin1 WW-domain binding to phosphoproteins (pSer) by phosphopeptides but not by nonphosphorylated (Ser) or proline-rich (Pro) peptides.

When Pin1 or its WW-domain were incubated with various concentrations (0, 25, 50, 125, 250, 500 μM) of Pintide or control peptide (C-Pintide) before incubation with mitotic extracts, the phosphoprotein-binding activity was significantly reduced in a concentration dependent manner by Pintide, but not with the nonphosphorylated peptide. (FIG. 1)

Pintide prevented Pin1 and its WW-domain from binding to phosphopeptide MPM2 antigens with similar affinity (Pin 1+pSer; WW+pSer; FIG. 1). Significant competition was detected at 50 μM, with a complete competition observed at 250–500 μM (FIG. 1). No competition between Pintide and WW-domain phosphopeptide binding was observed with increasing concentrations of proline-rich peptides (WW+Pro FIG. 1) or nonphosphorylated peptides (Pin1+Ser; WW+Ser; FIG. 1). These results demonstrate that a small phosphoserine-containing peptide, such as Pintide, can compete with phosphoproteins, not proline rich, binding to Pin1 or its WW-domain in a phosphorylation-dependent manner.

EXAMPLE 5

WW-Domains Bind Phosphopeptides with High Affinity

To determine the affinity of Pin1, and its WW or PPIase domain for phosphopeptides, peptides were labeled with fluorescein and their interactions with Pin1 measured using quantitative fluorescence anisotrophy. To prevent nonspecific labeling, a Pintide analogue (WFYpSPFLE) SEQ ID NO: 9 was used, which binds Pin1 with a high affinity based on the peptide library screen as described by (Lu, K. P. et al., U.S. Ser. No. 60/058,164 (1997), the teachings of which are incorporated herein in their entirety.

Pintide and its nonphosphorylated counterpart were synthesized and incubated with GST-Pin1 or the GST-WW-domain of Pin1 in a binding buffer, using established procedures (Shen, M. et al., Genes & Dev 12:706 (1998)). After a 1 hr incubation, mitotic HeLa cell extracts were added and subjected to GST pull down experiments, followed by immunoblotting analysis using the MPM-2 antibody. To obtain semi-quantitative data, films of immunoblots were scanned at the region of 55 kDa, the major Pin1-binding protein, and data analyzed using ImageQuan (ScanJet II CX). The peptide binding constants were measured using a fluorescence polarization assay (Jiskoot, W. et al., Anal Biochem 196:421 (1991)). Peptides were fluorescein labeled at the N-terminus using the Fluorescein Amine Labeling Kit (Pan Vera Corp.) and purified by TLC according to the manufacturer's interactions. To prevent nonspecific labeling, a Pintide analogue (WFYpSPFLE) SEQ ID NO: 8 and the nonphosphorylated control were used. Various concentrations of Pin1 and its mutant proteins were incubated with 0.1 μM of the labeled peptides in a binding buffer containing 50 mM HEPES, pH 7.4, 100 mM NaCl, 2% glycerol. Fluorescence polarization values were obtained using a Pan Vera Beacon 2000 system, as described by the manufacturer.

No binding was detected between Pintide and the PPIase domain or the nonphosphorylated control peptide and Pin1, its WW-domain or PPIase domain. Pin1 and its WW-domain bound Pintide (Tables 1 and 2). The WW-domain of Nedd4 bound Pintide with low affinity (Kd=10 μM) and did not bind the nonphosphorylated central peptide.

TABLE 2

Binding Constants of Mutant Proteins and Peptides

| Pin 1 Protein | WFYpSPFLE Kd(μM) | | WFYSPFLE |
|---|---|---|---|
| | High affinity | Low affinity | Kd |
| Pin1* | 1.2 | 11.0 | Not binding |
| WW-domain* | 1.0 | — | Not binding |
| PPIase Domain* | — | 15.0 | Not binding |
| GST-Pin1 | 1.2 | 13.0 | Not binding |
| GST-Pin1$^{Y23A}$ | — | 13.5 | N.D. |
| GST-Pin1$^{W34A}$ | — | 14.0 | N.D. |
| GST-Pin1$^{R14A}$ | 2.0 | 13.5 | N.D. |
| GST-Pin1$^{S16A}$ | 1.2 | 10.5 | N.D. |
| GST-Pin1$^{S16E}$ | — | 10.5 | N.D. |
| GST-Pin1$^{S18E}$ | 1.0 | 12.0 | N.D. |

The N-terminus of peptides (WFYpSPFLE, SEQ ID NO: 8; WFYSPFLE, SEQ ID NO: 9) was labeled with fluorescein-C6-amine labeling kit and purified by TLC (PanVera). Different concentrations of proteins as indicated as well as control GST were incubated with the labeled peptides and binding was measured by fluorescence aniostropy assay. Each value represents the average of three independent experiments. No binding was detected between Pin1 and the nonphosphorylated peptide or between GST and either peptide.
*, the N-terminal tag was cleaved from these proteins by thrombin.
N.D., not determined.

Pin1 displayed two binding sites for Pintide with high (Kd=1.2 μM) and low (Kd=11.0 μM) affinities (Table 2). The isolated WW-domain contained the high affinity binding site (Kd=1.2 μM) and the PPIase domain contained a low affinity (Kd=15.0 μM) binding site. These results demonstrate that both the WW-domain and the PPIase domain can bind the phosphopeptide; however, the binding affinity of the WW-domain is significantly higher (Kd=1.2 μM) than the binding affinity of the PPIase domain (Kd=15.0 μM). These data show that the WW-domain binds with high affinity to phosphopeptides and, specifically, a defined set of mitotic phosphoproteins. The interactions between WW-domains and target phosphoproteins are mediated by phosphoserine residues and protect dephosphorylation of ligands when bound to WW-domains. Therefore, the Pin1 WW-domain is a phosphoserine-binding module.

EXAMPLE 6

WW-Domain Mutants—Effects on Phosphoprotein Binding

Figure 2:
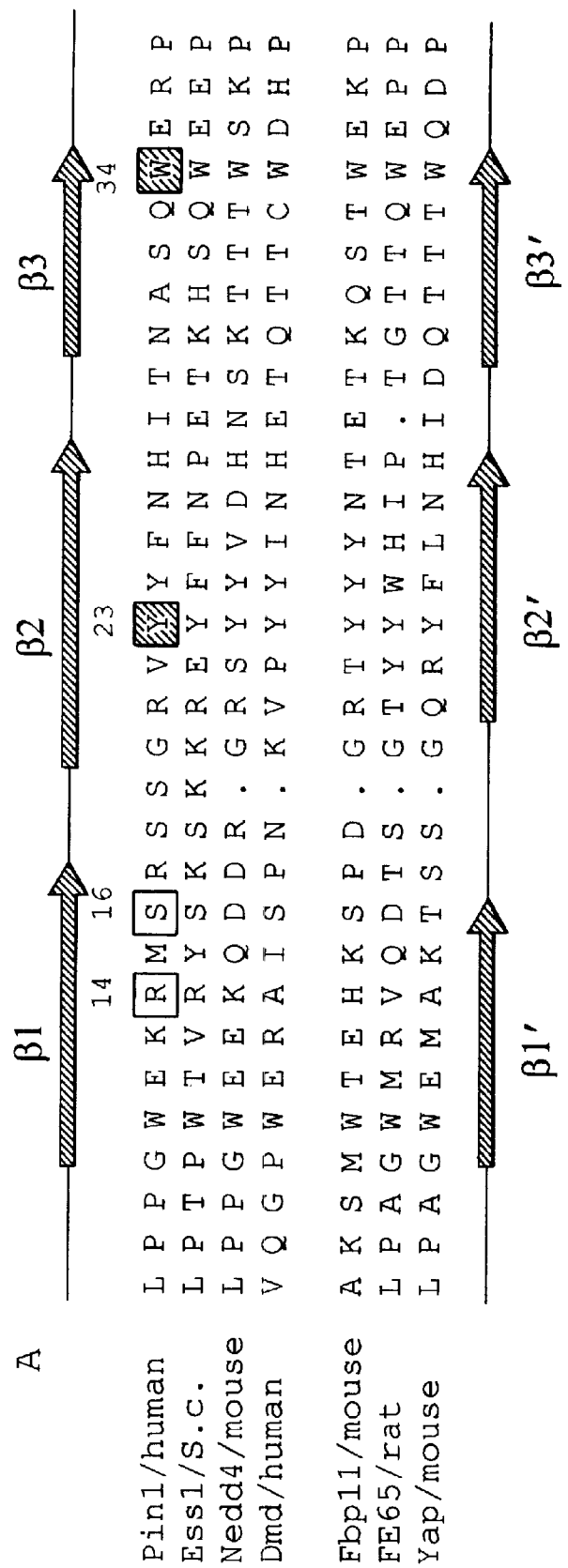
FIG. 2 is the amino acid sequence alignment of selected WW-domains. Pin1/human (SEQ ID NO: 1); Ess1/S.c. (SEQ ID NO: 2); Nedd4/mouse (SEQ ID NO: 3); Dmd/human (SEQ ID NO: 4); Fbp11/mouse (SEQ ID NO: 5); FE65/rat (SEQ ID NO: 6) and Yap/mouse (SEQ ID NO: 7).

To determine the structural basis for WW-domain-binding specificity, site-directed mutagenesis, followed by molecular modeling, was performed based on the Pin1 crystal structure (Macias, M. J. et al., Nature 382:646 (1996); Ranganathan, R. et al., Cell 89:875 (1997)). The PPIase domain, not the WW-domain of Pin1, contains a conserved basic patch in the active site, which is critical for recognition of phosphoserine (Yaffe, M. B. et al., Science 278:1957 (1997); Schutkowski, M. et al., Biochemistry 37:5566 (1998)). The WW-domain contains a hydrophobic cleft. A hydrophobic patch at the surface of a molecule often suggests a protein-protein interaction surface (Janin, J. et al., J. Biol. Chem. 265:16027 (1990); Clackson, T. et al., Science 267:383 (1995); Young, L. et al., Protein Sci. 3:717 (1994)). The hydrophobic cluster in the WW-domain of Pin1 sequesters a PEG molecule, which forms close contacts with Ser-16, Tyr-23 and Trp-34 located at three different strands of the anti-parallel β sheet, respectively (FIG. 2) (Macias, M. J. et al., Nature 382:646 (1996); Ranganathan, R. et al., Cell 89:875 (1997)).

A statistical analysis of phosphate binding sites in proteins ranks the propensity of Tyr to bind phosphate next only to that of Arg (Copley, R. R. et al., *J. Mol. Biol.* 242:321 (1994)). Thus, it is likely that Tyr-23 is important for WW-domain binding to phosphoserine. To examine whether this is the case, the WW-domain of Pin1 was mutated, using standard PCR mutagenesis techniques (Shen, M., et al., *Genes & Dev.* 12:706 (1998)), at Tyr-23 and Trp-34, as well as Arg-14, a residue close to Tyr-23 in the structure. Pin1 mutants were generated using PCR mutagenesis procedures (Shen, M. et al., *Genes & Dev* 12:706 (1998)). GST and (His)$_6$ fusion proteins containing Pin1 and various mutants were produced and tags cleaved using thrombin (Shen, M. et al., *Genes & Dev* 12:706 (1998)). The mutated Pin1 proteins were examined for their ability to bind phosphoproteins and peptides (Tables 2, 3 and 4).

Substitution of Arg-14 with Ala (Pin1$^{R14A}$) did not appear to cause a significant change in WW-domain to binding phosphopeptide or phosphoproteins, indicating that electrostatic interactions between Arg-14 in Pin1 are not essential for binding (Tables 2 and 3). In contrast, a single Ala point mutation of either Tyr-23 (Pin1$^{Y23A}$) or Trp-34 (Pin1$^{W34A}$) completely abolished the ability of Pin1 to bind either phosphoproteins or the phosphopeptide with high affinity, similar to the isolated PPIase domain (Tables 2, 3 and 4). These data indicate that Tyr-23 and Trp-34 are critical amino acids for the pSer-binding activity of the WW-domain.

TABLE 3

Binding Constants of WW-domain Mutants

| Protein | Kd for Pintide ($\mu$M) |
| --- | --- |
| Pin1 | 1.2 |
| Pin1$^{R14A}$ | 2.0 |
| Pin1$^{S16A}$ | 1.2 |
| Pin1$^{W34A}$ | N.B. |
| Pin1$^{Y23A}$ | N.B. |
| Pin1$^{Y23F}$ | 5.0 |

Different concentrations of various Pin1 proteins were incubated with the fluorescein labeled Pintide and binding constants measured by fluorescence aniostrophy assay. Each value represents the average of three independent experiments. Pin1 mutations only affected the Kd of the high affmity pSer-binding site in the WW-domain, not the low affinity pSer-binding site in the PPIase domain.

TABLE 4

Functional Properties of the WW-domain Mutants

| Pin 1 Protein | Phosphoprotein binding activity | PPlase Activity (%) | In vivo function |
| --- | --- | --- | --- |
| Pin1 | + | 100 | + |
| WW-domain | + | 0 | − |
| PPlase Domain | − | 90 | − |
| Pin1$^{Y23A}$ | − | 85 | − |
| Pin1$^{W34A}$ | − | 94 | − |
| Pin1$^{R14A}$ | + | 92 | + |
| Pin1$^{S16A}$ | + | 96 | + |
| Pin1$^{S16E}$ | − | 95 | − |
| Pin1$^{S18E}$ | + | 98 | + |
| Pin1$^{Y23F}$ | +/− | 94 | − |

Pin1 and Pin1 mutant proteins were expressed and purified as GST fusion proteins. The phosphoprotein-binding activity was assayed by incubating GST-fusion proteins with mitotic extracts, followed by immunoblotting analysis using the MPM2 antibody. +, binding was detected;, no binding was detected. PPIase activity was assayed using the peptide substrate (Schutkowski, M., et al., Biochemistiy 37:5566 (1998)) and represented relative to the activity of the wild-type protein defined as 100%. The in vivo function of Pin1 and its mutants was assayed by rescuing the temperature-sensitive ptf1 yeast mutant.

Tyrosine-mediated phosphorylation-dependent interactions have been reported between the phosphorylated KID domain of CREB and the KIX domain of the coactivator CBP (Radhakrishnan, I. et al., *Cell* 91:741–752 (1997)).

A pSer-Pro dipeptide was modeled into the hydrophobic cluster of the WW-domain in the place of the PEG molecule. Computer assisted molecular modeling based on co-ordinates of the Pin1 structure reported by Ranganathan et al., (*Cell* 89:875 (1997)), was performed using QUANTA on an SGI Indigo II workstation. Placement of the pSer-Pro dipeptide into the hydrophobic cleft of the WW-domain was determined by hydrophobic, hydrogen bonding and Van der Waals interactions. The Pro ring sits in a hydrophobic crevice stacked between the aromatic rings of Tyr-23 and Trp-34, whereas the pSer fits into a space between Ser-16 and Tyr-23, with the phosphate moiety being directed within hydrogen bonding distance of the Tyr-23 hydroxyl proton.

EXAMPLE 7

Pin1 Phosphorylation is Regulated In vivo

To determine whether Pin1 phosphoprotein-binding activity is regulated by Pin1 phosphorylation Pin1 mutants were constructed in regions of the WW-domain predicted to form the hydrophobic cleft. For example, if Ser-16 in the pSer-binding pocket was phosphorylated, a negatively charged residue can be introduced into the binding pocket and the phosphate group can form hydrogen bonding interactions with the side chain of Tyr-23. Phosphorylation of Ser-16 could prevent the Pin1 WW-domain from interacting with its ligand. To test this hypothesis, experiments were performed to determine whether Pin1 is a phosphoprotein and whether Pin1 phosphorylation is regulated during the cell cycle in vivo.

To detect in vivo phosphorylation of Pin 1, HeLa cells were arrested at the G1/S boundary or at mitosis in the presence of $^{32}$P orthophosphate (10 $\mu$Ci/ml) (Shen, M. et al., *Genes & Dev* 12:706 (1998)). The cells were lysed in RIPA buffer and subjected to immunoprecipitation using Pin1-specific antibodies, followed by separation on modified SDS-containing gels. For detecting a molecular weight shift of Pin1 during the cell cycle indicative of a change in the phosphorylation state of Pin1, HeLa cells were released from G1/S arrest for various times, the cell cycle analyzed by FACS and total lysates prepared in RIPA buffer were subjected to immunoblotting analysis using Pin1 antibodies, as previously described (Shen, M. et al., *Genes & Dev* 12:706 (1998)).

In vivo $^{32}$P-labeling experiments showed that Pin1 was hyperphosphorylated when cells were arrested at the G1/S boundary, mainly exhibiting as a single slow migrating species on SDS-gels. Pin1 was dephosphorylated when cells were arrested at mitosis, as indicated by the appearance of a fast migrating, lower molecular weight species of Pin1 on SDS-gels. To further determine the kinetics of Pin1 dephosphorylation during the cell cycle, HeLa cell lysates were collected at different times after release from the G1/S arrest and subjected to high resolution SDS-PAGE, followed by immunoblotting analysis using Pin1 antibody as described in Example 2. As shown previously (Shen, M. et al., *Genes & Dev* 12:706 (1998)), total Pin1 levels did not fluctuate during the cell cycle. However, two different molecular weight forms of Pin1 were detected. The faster migrating, lower molecular weight form of Pin1 was cell cycle-dependent, appearing only when cells were progressing through mitosis or when arrested at mitosis by nocodazole. These kinetic data are strongly correlated with the ability of Pin1 to bind phosphoproteins (Shen, M. et al., *Genes & Dev*

12:706 (1998)). These results show that the appearance of the fast migrating species of Pin1 is the dephosphorylated form of Pin1 and that Pin1 is phosphorylated in a cell cycle-regulated manner. Phosphorylation prevents Pin1 from interacting with phosphoserine ligands.

EXAMPLE 8

Phosphorylation of the WW-domain Prevents Interaction with Ligands

To examine the effect of Pin1 phosphorylation on Pin1 binding to ligands, Pin1 and Pin1 mutant proteins were incubated with the catalytic subunit of PKA and PKC (a mixture of $\alpha$, $\beta$ and $\gamma$, UBI) in a kinase reaction buffer containing 500 $\mu$M cold ATP at 30° C. for 15 min (Lu, K. P. et al., *Anal. Biochem.* 196:421 (1991)). The reactions were stopped by adding SDS sample buffer and reaction products separated on SDS-gels, followed by autoradiography. Pin1 proteins were isolated and used to bind MPM-2 antigens from mitotic extracts from HeLa cells, as previously described (Shen, M., et al., *Genes & Dev* 12:706 (1998)). Experiments were also performed with PKA and PKC, casein kinase, cyclin B/Cdc2 and SRPK1 kinases.

The kinases readily phosphorylated Pin1 and its WW-domain. More importantly, phosphorylation by PKA, but not PKC, completely abolished the interactions between Pin1 and MPM2 antigens or between WW-domain and MPM2 antigens. This is especially significant because Ser-16 in Pin1 is located in the PKA consensus phosphorylation site (KRXS) (Pearson, R. B. et al., *Methods in Enzymol.* 200:62–81 (1991)). These results indicate that phosphorylation of the WW-domains of Pin1 can prevent Pin1 from interacting with phosphorylated ligands.

To pinpoint the regulatory phosphorylation site in the Pin1 WW-domain, Ser-16 was mutated to Glu, a phosphorylatable amino acid residue. The resulting mutant (Pin1$^{S16E}$) protein failed to bind mitotic phosphoproteins. Furthermore, no high affinity-binding site for the phosphoserine peptide was detected in Pin1$^{S16E}$ (Tables 2, 3 and 4). These results indicate that the S16E mutation completely abolishes the ability of the Pin1 WW-domain to bind its ligands, as is the case of PKA phosphorylation. As a control, a nearby Ser residue, Ser-18, was mutated to Glu (Pin1$^{S18E}$). The Pin1$^{S18E}$ mutation did not affect the ability of Pin1 to bind phosphoproteins or Pintide peptide (Tables 2, 3 and 4). These results indicate that Ser-16 is a critical phosphorylation site that regulates interactions between Pin1 and phosphoproteins.

Since PKA phosphorylated Pin1 on multiple sites as detected by phosphopeptide analysis, further experiments were performed to determine whether Ser-16 is the critical phosphorylation site that regulates phosphoprotein binding. Ser-16 was substituted with Ala, a nonphosphorylatable amino acid residue, and the mutant protein was used to bind MPM-2 antigens and the Pintide analogue. Similar to wild-type Pin1, the Pin1$^{S16A}$ mutant interacted with all Pin1 ligands and the Pintide peptide (Tables 2, 3 and 4), indicating that Ala is able to substitute for Ser-16 to fulfill the spatial requirement for the binding. More importantly, the interactions of Pin1$^{S16A}$ with phosphoproteins or the Pintide analogue were not affected by PKA phosphorylation (Tables 2, 3 and 4), although the mutant protein could still be phosphorylated by PKA. These results confirm that phosphorylation on Ser-16 is both necessary and sufficient to regulate the interaction between Pin1 and phosphoproteins. Thus, the interaction between Pin1 and its ligands is tightly regulated, depending on phosphorylation of ligands as well as dephosphorylation of the pSer-binding pocket of its WW-domain.

EXAMPLE 9

Phosphoprotein-binding Activity of the WW-domain of Pin1 is Essential for the In vivo Function of Pin1

Given the essential role of the WW-domain in conferring Pin1-binding specificity in vitro, a critical question is whether this domain is important in vivo. To address this question, experiments using the PIN1 yeast homologue, ESS1/PTF1 were performed. ESS1/PTF1 is essential for cell growth and human Pin1 can carry out this essential function when transfected into yeast cells (Lu, K. P. et al., *Nature* 380:544 (1996); Hanes, S. D. et al., *Yeast* 5:55 (1989); Hani, J. et al., *FEBS Lett.* 365:198 (1995)). A temperature-sensitive ptf1 mutant strain, YPM2, grows at the permissive temperature (23° C.), but not at the restrictive temperature (30° C.) (Hanes, S. D. et al., *Yeast* 5:55 (1989); Hani, J. et al., *FEBS Lett.* 365:198 (1995)). This phenotype is completely rescued by a 1.5 kb PTF1 genomic fragment, which also contains the promoter and the 3' processing sequence (FIG. 3). To insure that all human Pin1 proteins were expressed at physiological levels under normal regulation, the coding sequence of the fully functional ESS1/PTF1 gene in a Yepvector was replaced with the coding sequence of the human PIN1 (or Pin1 mutant) cDNA (FIG. 3) and transformed into a temperature-sensitive ptf1 strain. Transformants were selected on minimal media minus Leu at the permissive temperature (23° C.) and protein expression was detected by immunoblotting analysis using 12CA5 monoclonal antibody specific for the HA epitope tag inserted at the N-terminus. The HA tag does not affect the Pin1 function (Lu, K. P. et al., *Nature* 380:544 (1996)). Those strains expressing similar levels of Pin1 and Pin1 mutants were grown at permissive and nonpermissive temperature. At least 3–4 strains were tested for each construct, with similar results.

When transformed into YPM2 cells, the human Pin1 fully complemented the temperature-sensitive phenotype, indicating that human Pin1 is fully functional when expressed under the endogenous promoter. To determine whether the WW-domain is important for Pin1 to exert its essential function, the WW-domain and the PPIase domain of Pin1 were individually expressed at a similar level to the whole length protein (Table 4). These results indicate that the WW-domain is indispensable in vivo. To further confirm this observation, various WW-domain point mutants were introduced into YPM2 strains using the same expression vector and expressed at levels similar to that of wild type protein in cells. The WW-domain mutants that were able to bind phosphoproteins rescued the ptf1 phenotype (Table 4). However, Pin1 mutations, including S16E, Y23A, W34A, which disrupt interactions between the WW-domain and phosphoproteins, abolish the ability of Pin1 to support cell growth. These results demonstrate that phosphoprotein-binding activity of the WW-domain is essential for the in vivo propyl-peptidyl cis-trans isomerase activity of Pin1.

EXAMPLE 10

Interaction Between Pin1 WW-Domain and Phosphorylated tau and Amyloid Precursor Protein Peptides The interaction between Pin1 and tau proteins, which are heavily phosphorylated at mitosis and in Alzheimer's disease, were examined. Pin1 bound phosphorylated tau and colocalized with tau at paired helical filaments in brain sections of patients with Alzheimer's disease. To map the Pin1-binding site in tau or amyloid proteins, Pin1 or its WW-domain mutants were incubated with phosphorylated (pT, pS) or nonphosphorylated (S,T) peptides derived from tau or amyloid protein, followed by measuring peptide binding using ELISA assay. Pin1 bound with high affinity (Kd=25 nM) only the phosphorylated Thr-231 tau peptide, an interaction mediated by the Pin1 WW-domain as the Pin1$^{R14A}$, but not Pin1$^{Y23A}$ Table 5; FIG. 4B. The Pin1 WW-domain also specifically bind phosphorylated Thr-668 amyloid precursor protein peptide (Table 5).

A lower affinity binding constant was obtained with ELISA assays compared to fluorescence aniostropy assays. This might be due to the following reasons: 1) peptides are oriented at the same direction in ELISA assay, but not in aniostrophy assay; 2) ELISA assay is more sensitive than aniostrophy assay; and/or 3) different peptides have different affinities. In any case, the Pin1 WW-domain mediates specific interaction between Pin1 and tau or amyloid proteins.

TABLE 5

Specific Interaction between the Pin1 WW-domain and a Phosphoiylated Tau Peptide

|  | SEQ ID NO. | Tau Peptides |  | Binding (OD@405 nm) |
|---|---|---|---|---|
| Pin1 | 15 | DAGLKESPLQTPTE | (pS-46) | 0.00 |
|  | 16 | TRIPAKTPPAPKT | (pT-175) | 0.00 |
|  | 17 | GYSSPGSPGTPGSR | (pS-202) | 0.08 |
|  | 18 | SRSRTPSLPTPPT | (pS-214) | 0.00 |
|  | 19 | KVAVVRTPPKSPS | (T-231) | 0.00 |
|  | 20 | KVAVVRTPPKSPS | (pT-231) | 1.46 |
|  | 21 | VRTPPKSPSSAKSR | (pS-235) | 0.11 |
|  | 22 | VQSKIGSLDNITH | (pS-356) | 0.00 |
|  | 23 | GSLDNITHVPGGG | (pT-361) | 0.00 |
|  | 24 | TSPRHLSNVSSTG | (pS-409) | 0.00 |
|  | 25 | PRHLSNVSSTGSIDMV | (pS-412) | 0.02 |
|  | 26 | PRHLSNVSSTGSIDMV | (pS-413) | 0.00 |
|  | 27 | NVSSTGSIDMVDS | (pS-416) | 0.00 |
|  | 28 | SIDMVDSPQLATL | (pS-422) | 0.00 |
| Mutant |  |  |  |  |
| Pin1$^{R14A}$ | 29 | KVAVVRTPPKSPS | (pT-231) | 1.30 |
| Pin1$^{Y23A}$ | 30 | KVAVVRTPPKSPS | (pT-231) | 0.00 |
|  |  | Amyloid Precursor Protein Peptide |  |  |
|  | 31 | KEVDAAVTPEERHLS | (T-668) | 0.00 |
|  | 32 | KEVDAAVTPEERHLS | (pT-668) | 1.81 |

EXAMPLE 11

Functional Restoration of Alzheimer Phosphorylated tau by the WW-Domain of Pin1

A neuropathological hallmark in Alzheimer's disease is the neurofibrillary tangle, the main components of which are paired helical filaments (PHFs) composed of the microtubule-associated protein tau (Lee, V. M. Curr Opin Neurobiol 5:663–668 (1995); Mandelkow, E. et al., Neurobiol Aging 16:347–354 (1995); Kosik, K. S. et al., Ann N Y Acad Sci 777:114–120 (1996); Spillantini, M. G. and Goedert, M. Trends Neurosci 21:428–433 (1998) and Iqbal, K. et al., J Neural Transm Suppl 53:169–180 (1998)). Tau is hyperphosphorylated in PHFs (Lee, V. M. et al., Science 251:675–678 (1991); Goedert, M. et al., Neuron 8:159–168 (1992); Greenberg, S. G. et al., J Biol Chem 267:564–569 (1992)) and phosphorylation of tau causes loss of its ability to bind microtubules and promote microtubule assembly (Bramblett, G. T. et al., Neuron 10:1089–1099 (1993); Yoshida, H. and Ihara, Y. J Neurochem 61:1183–1186 (1993); Iqbal, K. et al., FEBS Lett 349:104–108 (1994)). Restoring the function of phosphorylated tau could prevent or reverse PHF formation in Alzheimer's disease.

Phosphorylation on serines or threonines that precede proline (Ser/Thr-Pro) alter the prolyl isomerization rate and create a binding site for the prolyl isomerase Pin1 (Lu, K. P. et al., Nature 380:544–547 (1996); Yaffe, M. B. et al., Science 278:1957–1960 (1997); Shen, M. et al., Genes Dev. 12:706–720 (1998); Schutkowski, M. et al., Biochemistry 37:5566–5575 (1998); Crenshaw, D. G. et al., S. Embo J 17:1315–1327 (1998)). Pin1 specifically isomerizes phosphorylated Ser/Thr-Pro bonds and regulates the function of several mitotic phosphoproteins (Lu, K. P. et al., Nature 380:544–547 (1996); Yaffe, M. B. et al., Science 278:1957–1960 (1997); Shen, M. et al., Genes Dev. 12:706–720 (1998)).

The following data show that Pin1 binds a specific phosphorylated Thr-Pro motif in tau. Pin1 colocalizes and copurifies with PHFs, and soluble Pin1 is significantly depleted in brains of patients with Alzheimer disease. Furthermore, Pin1 fully restores the ability of phosphorylated tau to bind microtubules and promote microtubule assembly in vitro. Thus, Pin1 is the first molecule that can restore the biological activity of phosphorylated tau without dephosphorylation. In addition, since depletion of Pin1 induces mitotic arrest and apoptosis (Shen, M. et al., Genes Dev. 12:706–720 (1998)), sequestration of Pin1 into PHFs in Alzheimer's disease can contribute to neuronal loss.

Pin1 Binds and Regulates Mitotic Phosphoproteins

Pin1 binds and regulates the function of a defined subset of mitotic phosphoproteins by interacting with conserved phosphorylated Ser/Thr-Pro motifs that are also recognized by MPM-2, a mitosis-specific, phosphorylation-dependent monoclonal antibody (mAb) (Yaffe, M. B. et al., Science 278:1957–1960 (1997); Shen, M. et al., Genes Dev. 12:706–720 (1 998)). Tau is an MPM-2 antigen phosphorylated on multiple Ser/Thr-Pro motifs during mitosis (Illenberger, S. et al., Mol Biol Cell 9:1495–1512 (1998)). Experiments were undertaken to determine whether Pin1 binds tau. Tau isoform was either synthesized by in vitro transcription and translation in the presence of $^{35}$S-Met or produced in bacteria as an N-terminal His-tagged protein, followed by purification using NTA-Ni columns (Yaffe, M. B. et al., Science 278:1957–1960 (1997); Shen, M. et al., Genes Dev. 12:706–720 (1998)). To generate interphase- and mitosis-specific phosphorylated form of tau, tau was incubated with Xenopus interphase and mitotic extracts, respectively (Shen, M. et al., Genes Dev. 12:706–720 (1998)). To prepare Cdc2 phosphorylated tau, purified recombinant tau was incubated with purified cyclin B/Cdc2 (UBI) for 6 to 12 hr at room temperature in a buffer containing 500 μM cold ATP, plus trace [$^{32}$P]-ATP in some experiments, (Vincent, I. et al., J Neurosci 17:3588–3598 (1997)).

Pin1 did not bind tau incubated with interphase Xenopus extracts, but did bind tau that was phosphorylated by mitotic extracts. Mitotic binding between Pin1 and tau was abolished when mitotically phosphorylated tau was dephosphorylated by alkaline phosphatase. These results indicate that Pin1 binds phosphorylated tau in a mitosis-specific and phosphorylation-dependent manner, as shown for many other Pin1-binding proteins (Shen, M. et al., Genes Dev. 12:706–720 (1998)), including Cdc25.

Mitotic events are aberrantly activated in the Alzheimer's disease brain, including re-expression of Cdc2 kinase and cyclin B (Vincent, I. et al., *J Cell Biol* 132:413–425 (1996); Vincent, I. et al., *J Neurosci* 17:3588–3598 (1997); Nagy, Z. et al., *Acta Neuropathol* 94:6–15 (1997); Nagy, Z. et al., *Acta Neuropathol* (Berl) 93:294–300 (1997)). The phosphorylation pattern of tau in mitotic cells is strikingly similar to that in Alzheimer's disease (AD) brains, as detected by phosphorylation site-specific tau mAbs (Illenberger, S. et al., *Mol Biol Cell* 9:1495–1512 (1998); Vincent, I. et al., *J Cell Biol* 132:413–425 (1996); Vincent, I. et al., *J Neurosci* 17:3588–3598 (1997); Kondratick, C. M. and Vandre, D. D. *J Neurochem* 67:2405–2416 (1996); Vincent, I. et al., *Neurobiol Aging* 19:287–296 (1998); Preuss, U. and Mandelkow, E. M. *Eur J Cell Biol* 76: 176–184 (1998)). Mitotically phosphorylated tau is recognized by AD-specific, phosphorylation-dependent tau mAbs, including CP9, TG3 and PHF1 (Illenberger, S. et al., *Mol Biol Cell* 9:1495–1512 (1998); Vincent, I. et al., *J Cell Biol* 132:413–425 (1 996); Vincent, I. et al., *J Neurosci* 17:3588–3598 (1997)); Kondratick, C. M. and Vandre, D. D. *J Neurochem* 67:2405–2416 (1996); Vincent, I. et al., *Neurobiol Aging* 19:287–296 (1998); Preuss, U. and Mandelkow, E. M. *Eur J Cell Biol* 76: 176–184 (1998)). These results indicate that common Ser/Thr-Pro motifs of tau are phosphorylated in normal mitotic cells and in Alzheimer brains. Thus, Pin1 can bind and regulate the function of tau in AD.

Pin1 Interactions with tau in Extracts of Brains from Alzheimer's Patients

Pin1 interactions with tau in AD brains were examined using a GST-Pin1 pulldown assay (Shen, M. et al., *Genes Dev.* 12:706–720 (1998)). Glutathione beads containing GST or GST-Pin1 were incubated with normal or AD brain extracts, or PHFs purified (Vincent, I. J. and Davies, P. *Proc Natl Acad Sci USA* 89:2878–2882 (1992)), and proteins associated with the beads were subjected to immunoblotting analysis using CP27, which recognizes all forms of tau. Recombinant and mutant Pin1 proteins were produced as N-terminal GST or His-tagged fusion proteins (Shen, M. et al., *Genes Dev.* 12:706–720 (1998)). PHFs were purified by immunoaffinity chromatography (Vincent, I. J. and Davies, P. *Proc Natl Acad Sci USA* 89:2878–2882 (1992)). Pin1 antibodies and tau mAbs (CP27, TG3, PHF1 and CP9) were used as previously described (Shen, M. et al., *Genes Dev.* 12:706–720 (1998); Jicha, G. A. et al., *J Neurochem* 69:2087–2095 (1997)).

For determining the level of soluble Pin1, brain tissues were sliced, cut into fine pieces and homogenized in buffer A (50 mM Hepes, pH 7.4, 150 mM NaCl, 10% glycerol, 1% Triton X-100, 5 mM $MgCl_2$, 1 mM EGTA, 1 mM DTT, 100 mM NaF, 2 mM $Na_3VO_4$ and various protease inhibitors). The homogenates were centrifuged at 100,000 g at 4° C. for 30 min and the supernatants were directly used for immunoprecipitations or immunoblotting analysis using Pin1 antibodies described (Shen, M. et al., *Genes Dev.* 12:706–720 (1998)) or stored in aliquots at −80° C. before assays.

GST-Pin1, but not control GST, bound tau present in AD brain extracts or PHFs. In contrast, Pin1 did not bind tau in age-matched normal brain extracts. These results indicate that Pin1 interacts with the AD-specific tau in vitro. To determine whether Pin1 forms a stable complex with AD tau in vivo, PHFs were purified using affinity chromatography (Vincent, I. J. and Davies, P. *Proc Natl Acad Sci USA* 89:2878–2882 (1992)), and dissolved in SDS sample buffer, following by immunoblotting analysis using anti-Pin1 antibodies. Pin1 was detected in PHFs purified from all 6 AD brains examined. These results indicate that Pin1 co-purifies with PHFs.

Immunocytochemical Localization of Pin1 in Alzheimer and Normal Brains

To further confirm that Pin1 has specific affinity for PHFs, recombinant Pin1 was added onto brain sections, washed, and then subjected to immunostaining using affinity purified Pin1 antibodies to localize bound Pin1. To localization exogenously added Pin1 in brain sections, 50 μm sections were cut from formalin fixed frontal cortex or hippocampus of human brains, endogenous peroxidase activity blocked with $H_2O_2$, followed by incubation with Pin1 at 0.5 μM. The sections were incubated with the mAb TG3 or anti-Pin1 antibodies that had been purified using GST-Pin1 glutathione beads, and visualized by the immunoperoxidase staining protocol, to detect endogenous Pin1, fixed brain sections were first microwaved in an antigen retrieval buffer (Biogenex), as described by the manufacturer, then subjected to immunostaining procedure.

When recombinant Pin1 was not added to normal or AD brain sections, no immunoreactive signal was observed, indicating that the Pin1 antibodies do not recognize endogenous Pin1. However, if Pin1 was added to normal and AD brain sections, dramatically different results were observed. Although Pin1 binding signal was not detected in normal brain sections, Pin1 binding signals were detected in the cytoplasm of neurons in AD brain sections. Specifically, Pin1 strongly bound neurofibrillary tangles and neurites, as shown by co-immunostaining with TG3, which recognizes the AD-specific conformation of tau phosphorylated on threonine-231 (T231) (Jicha, G. A. et al., *J Neurochem* 69:2087–2095 (1997)). These results demonstrate that exogenous Pin1 specifically binds the neurofibrillary tangles in neurons.

Given that Pin1 has a high affinity for the tangles and purifies with PHFs, it is critical to examine the in vivo relationship between Pin1 and PHFs. To address this question, fixed brain sections were subjected to an antigen retrieval procedure. Strong immunoreactivity was observed with Pin1 antibodies in both normal and AD brain sections. To ensure that these signals represent Pin1, the Pin1-specific antibodies were first depleted using GST-Pin1 beads and then used for immunostaining. Pin1-depleted antibodies showed no specific immunoreactivity with either normal or AD brain sections. Strikingly different patterns of Pin1 localization were observed in normal and AD brain sections. Pin1 was localized primarily in nuclei of neurons in normal brain sections and in neuronal nuclei in AD brain sections. These results are consistent with the findings that both ectopically expressed and endogenous Pin1 is primarily localized in the nucleus in HeLa cells (Lu, K. P. et al., *Nature* 380:544–547 (1996)).

However, in AD brains, intense Pin1 immunostaining were observed in the cytoplasm of neurons, specifically at the tangle structure that was also recognized by TG3 (Jicha, G. A. et al., *J Neurochem* 69:2087–2095 (1997)). These results indicate that both exogenous and endogenous Pin1 specifically localize to the neurofibrillary tangles in AD brains.

Binding of Pin1 to PHFs could trap Pin1 in the tangles, eventually leading to depletion of the soluble Pin1 in neurons. To test this possibility, the levels of Pin1 and two tau kinases, GSK3b and Cdc2, were compared in AD and normal brain tissues. Brain tissues were homogenized and soluble proteins were directly subjected to immunoblotting analysis, followed by semi-quantification of protein levels using ImageQuan. When compared with 6 age-matched normal brains, GSK3b levels were slightly reduced (40±11%), and Cdc2 levels were significantly increased by approximately 5 fold in AD brains (547±87%, n=6, P<0.01). These findings are consistent with previous studies showing that levels of Cdc2, but not GSK3b, are abnormally elevated in Alzheimer's disease brains (Vincent, I. et al., *J Neurosci* 17:3588–3598 (1997)).

The levels of soluble Pin1 in AD brains was lower than in normal brains, with the average reduced by approximately 5 fold (22.4±3.4%). This decrease in Pin1 levels was confirmed by Pin1 immunoprecipitation analysis. These data show that soluble Pin1 is significantly reduced in brains from human suffering from Alzheimer's disease. Therefore, Pin1 can be a potential gene therapy target.

Identification of Pin1 Binding Sites in tau

The interaction between Pin1 and mitotic phosphoproteins is mediated by the Pin1 N-terminal WW-domain, which acts as a phosphoserine-binding module interacting with specific phosphorylated Ser/Thr residues in ligands (Examples 1–10). To identify the Pin1 binding site(s) in tau, phosphorylated and nonphosphorylated peptides that cover previously identified tau phosphorylation sites, were assayed for their ability to bind Pin1 by ELISA (Jicha, G. A. et al., *J Neurochem* 69:2087–2095 (1997)). Pin1 exhibited specific and high affinity binding to a tau peptide containing phosphorylated threonine-231 (pT231 tau peptide), with the dissociation constant of ≈40 nM (FIG. 4A). No binding was observed between Pin1 and the non-phosphorylated counterpart (FIG. 4A), demonstrating an absolute requirement of T231 phosphorylation for Pin1 binding. To determine whether the N-terminal WW-domain of Pin1 is responsible for binding, the mutant $Pin1^{Y23A}$ (Example 6) was used. The $Pin1^{Y23A}$ mutant contains a single Ala substitution at the critical Tyr-23 in the WW-domain, resulting in a complete lose of the phosphoserine-binding activity (Example 6). No binding between $Pin1^{Y23A}$ and pT231 tau peptide was detected (Table 5). Collectively, these results show that Pin1 specifically binds the motif containing the pT231 residue in tau through its WW-domain.

Phosphorylation of tau on T231 (pT231-tau) has been well documented in AD brains and can be recognized by several mAbs, including CP9 (Illenberger, S. et al., *Mol Biol Cell* 9:1495–1512 (1998); Vincent, I. et al., *J Neurosci* 17:3588–3598 (1997); Preuss, U. and Mandelkow, E. M. *Eur J Cell Biol* 76: 176–184 (1998); Jicha, G. A. et al., *J Neurochem* 69:2087–2095 (1997); Billingsley, M. L. and Kincaid, R. L. *Biochem J* 323:577–591 (1997)). To determine whether Pin1 interacts with pT231-tau, GST-Pin1 beads were used to isolate tau from AD brain extracts or PHFs and T231 phosphorylation detected using CP9. Tau isolated by Pin1 beads was strongly immunoreactive with CP9. These result indicate that phosphorylation of tau on T231 results in tau binding to Pin1 and that Pin1 binding does not result in dephosphorylation of pT231-tau. Since T231 in tau is readily phosphorylated by Cdc2 kinase in vitro (Vincent, I. et al., *J Cell Biol* 132:413–425 (1996); Vincent, I. et al., *J Neurosci* 17:3588–3598 (1997); Jicha, G. A. et al., *J Neurochem* 69:2087–2095 (1997)), experiments were performed to determine whether Pin1 binds tau that is phosphorylated by Cdc2 in vitro. Pin1 and its WW-domain, but not its PPIase domain, bound Cdc2 phosphorylated tau. Thus, Pin1 binds pT231-tau through its WW-domain. These data are consistent with Pin1 binding to mitotically phosphorylated tau and sequestration of Pin1 in PHFs of AD brains where Cdc2 is abnormally upregulated.

Pin1 Interactions with tau Promote Binding of tau to Microtubules

The high affinity interaction between Pin 1 and phosphorylated tau can affect the biological activity of tau. Upon phosphorylation by many protein kinases, including Cdc2, tau loses its ability to bind microtubules (MTs) and promote MT assembly (Bramblett, G. T. et al., *Neuron* 10:1089–1099 (1993); Iqbal, K. et al., *FEBS Lett* 349:104–108 (1994); Yoshida, H. and Ihara, Y. *J Neurochem* 61:1183–1186 (1993); Alonso, A. C. et al., *Proc Natl Acad Sci USA* 91:5562–5566 (1994); Busciglio, J. et al., *Neuron* 14:879–888 (1995)) although the exact mechanism is not fully understood. To determine whether Pin1 can restore the ability of phosphorylated tau to bind MTs, phosphorylated tau was produced using purified Cdc2 (Vincent, I. et al., *J Cell Biol* 132:413–425 (1996); Vincent, I. et al., *J Neurosci* 17:3588–3598 (1997)) and assessed for its ability to bind Taxol-stabilized MTs in the presence or absence of Pin1. Phosphorylation of tau by Cdc2 prevented tau from binding MTs, whereas binding was restored by incubation with Pin1. Pin1 was detected in the fraction of tau-bound MTs confirming interaction between Pin1 and phosphorylated tau. These data demonstrate that Pin1 binds phosphorylated tau and restores its ability to bind MTs.

The effect of Pin1 on the ability of phosphorylated tau to promote MT assembly was determined using light-scattering assays (Bramblett, G. T. et al., *Neuron* 10:1089–1099(1993); Alonso, A. C. et al., *Proc Natl Acad Sci USA* 91:5562–5566 (1994); Busciglio, J. et al., *Neuron* 14:879–888 (1995)). Briefly, MTs were assembled from phosphocellulose purified bovine tubulin (Cytoskeleton, Inc) and stabilized by Taxol. The nonphosphorylated or Cdc2 phosphorylated recombinant tau (0.1 mg/ml) was incubated with Pin1 (0.1 mg/ml) at 35° C. for 5 min before adding to the MTs. Bound tau was isolated by centrifugation (50,000×g) at 25° C. for 20 min, followed by immunoblotting analysis using CP27 and Pin1 antibodies. The ability of tau to promote MT assembly was determined using well established light-scattering assays. Briefly, the assembly of MTs was initiated by incubating tubulin (2 mg/ml) with or without tau (0.05 mg/ml) in 80 mM PIPES, pH 6.8, 1 mM EGTA, 1 mM $MgCl_2$, 1 mM GTP, 20% glycerol at 35° C. for 2 min. The mixture was then transferred to a 100 μl cuvet and the rate of the MT assembly was monitored at room temperature using the turbidity increase at 350 nm. To examine the effect of Pin1, Pin1 or its mutant (0.05 mg/ml) was pre-incubated with tau or Cdc2 phosphorylated tau (0.05 mg/ml) at 35° C. for 5 min before the MT assembly assays. Each experiment was repeated at least three times, with similar results being observed. Results using GST-Pin1 or His-Pin1 were similar, indicating that the N-terminal tags have no effect on the MT assembly assayed.

The rate of the turbidity change was minimal in the absence of tau, but was dramatically increased when recombinant tau was added to the mixture (FIG. 5A). However, this rate of the increase was substantially abolished if tau was phosphorylated by Cdc2 (FIG. 5B). These results show that phosphorylation of tau by Cdc2 disrupts its ability to promote MT assembly. Although Pin1 had no effect on the ability of nonphosphorylated tau to promote MT assembly, Pin1 restored the ability of Cdc2 phosphorylated tau to promote MT assembly (FIG. 5B). In contrast, the $Pin1^{Y23A}$ mutant did not have any effect on the microtubule assembly promoting effects of phosphorylated tau, indicating that the interaction is essential for Pin1 to regulate the function of phosphorylated tau. The MT assembly rate induced by phosphorylated tau in the presence of Pin1 was slightly higher than that induced by recombinant tau consistent with previous studies demonstrating that a certain degree of tau phosphorylation is required for its maximal activity to promote tubulin assembly (Iqbal, K. et al., *FEBS Lett*

349:104–108 (1994); de Ancos, J. G. et al., *J Biol Chem* 268:7976–7982 (1993)). Therefore, that Pin1 not only binds phosphorylated tau, but also functionally restores its biological activity.

Tau protein normally stabilizes the internal microtubular structure of neurons that functions to transport proteins and other molecules through the cells (Lee, V. M. *Curr Opin Neurobiol* 5:663–668 (1995); Mandelkow, E. et al., *Neurobiol Aging* 16:347–354 (1995); Kosik, K. S. et al., *Ann N Y Acad Sci* 777:114–120 (1996); Spillantini, M. G. and Goedert, M. *Trends Neurosci* 21:428–433 (1998); Iqbal, K. et al., *J Neural Transm Suppl* 53:169–180 (1998)). The importance of tau for neural function has been demonstrated by the recent findings that mutations in tau cause hereditary forms of frontal-temporal dementia (FTDP-17) (Clark, L. N. et al., *Proc Natl Acad Sci USA* 95:13103–13107 (1998); Spillantini, M. G. and Goedert, M. *Trends Neurosci* 21:428–433 (1998); Hutton, M. et al., *Nature* 393:702–705 (1998); Poorkaj, P. et al., *Ann Neurol* 43:815–825 (1998)). The signature lesions in FTDP-17 brains are aggregates composed of hyperphosphorylated tau, similar to those in brains of AD patients (Spillantini, M. G. et al., *Brain Pathol* 8:387–402 (1998); Reed, L. A. et al., *J Neuropathol Exp Neurol* 57:588–601 (1998)). Certain FTDP-17 mutations also disrupt the ability of tau to bind MTs and promote MT assembly (Hong, M. et al., *Science* 282:1914–1917 (1998); Hasegawa, M. et al., *FEBS Lett* 437:207–210 (1998)), suggesting that the interaction between tau and MTs is critical for the normal function of neurons. Furthermore, the absence of senile plaques and Lewy bodies in FTDP-17 (Spillantini, M. G. et al., *Brain Pathol* 8:387–402 (1998); Reed, L. A. et al., *J Neuropathol Exp Neurol* 57:588–601 (1998)) suggests that the tau pathology in AD may not be simply a secondary effect of the disease process, but rather can directly lead to neuronal loss.

Although it is established that most neurons in normal adult brains are postmitotic and lack mitotic kinase activity (Rakie, P. *Ann. NY. Acad. Sci.* 457:193–211 (1985); Nagy, Z. et al., *Neuroscience* 87:731–739 (1998)), several studies have shown that mitotic events are abnormally activated in neurons in AD brains (Vincent, I. et al., *J Cell Biol* 132:413–425 (1996); Vincent, I. et al., *J Neurosci* 17:3588–3598 (1997); Nagy, Z. et al., *Acta Neuropathol* 94:6–15 (1997); Nagy, Z. et al., *Acta Neuropathol* (Berl) 93:294–300 (1997)). Similar patterns of phosphoepitopes are observed in mitotic cells and AD neurons and mitotic phosphoepitopes appear before paired helical filaments (Illenberger, S. et al., *Mol Biol Cell* 9:1495–1512 (1998); Vincent, I. et al., *J Cell Biol* 132:413–425 (1996); Vincent, I. et al., *J Neurosci* 17:3588–3598 (1997); Kondratick, C. M. and Vandre, D. D. *J Neurochem* 67:2405–2416 (1996); Vincent, I. et al., *Neurobiol Aging* 19:287–296 (1998); Preuss, U. and Mandelkow, E. M. *Eur J Cell Biol* 76:176–184 (1998)). Therefore, it is proposed that aberrant activation of mitotic events in neurons can contribute to hyperphosphorylation of tau and formation of PHFs (Nagy, Z. et al., *Neuroscience* 87:731–739 (1998)). This hypothesis is further supported by the above identified described data which show that the essential mitotic regulator Pin1 binds the common phosphorylated motif of tau present in mitotic cells and AD brains.

Pin1 can restore the ability of phosphorylated tau to bind MTs and promote MT assembly. This binding provides the first example of restoration of the biological activity of phosphorylated tau without dephosphorylation. Since Pin1 is able to bind phosphorylated Ser/Thr-Pro motifs as well as to isomerize the phosphorylated Ser/Thr-Pro peptide bonds using its N-terminal and C-terminal domains, respectively, it is conceivable that Pin1 regulates the tau function by altering the conformation of the phosphorylated Ser/Thr-Pro motif(s).

Pin1 inhibits entry into mitosis and directly inhibits activation of Cdc25 (Lu, K. P. et al., *Nature* 380:544–547 (1996); Shen, M. et al., *Genes Dev.* 12:706–720 (1998)), a key mitosis-inducing phosphatase that removes the inhibitory phosphates from Cdc2 (Nurse, P. *Cell* 79:547–550 (1994); King, R. W. et al., *Cell* 79:563–571 (1994)). Thus, Pin1 can prevent abnormal activation of mitotic events in neurons and control the function of phosphoproteins, such as tau, in case they are phosphorylated due to transient and aberrant activation of Pro-directed kinases. However, a long-term and sustained activation of mitotic events would result in continuous hyperphosphorylation of tau, which binds and sequesters Pin1, as seen during the development of AD. This leads to at least two potential consequences. First, hyperphosphorylation of tau may create more binding sites than the capacity of the available Pin1, as suggested by the finding that PHFs have extra binding sites for exogenous Pin1. In this case hyperphosphorylated tau is not able to bind MTs and subsequently forms PHFs, affecting the normal function of neurons (Lee, V. M. *Curr Opin Neurobiol* 5:663–668 (1995); Mandelkow, E. et al., *Neurobiol Aging* 16:347–354 (1995); Kosik, K. S. et al., *Ann N Y Acad Sci* 777:114–120 (1996); Spillantini, M. G. and Goedert, M. *Trends Neurosci* 21:428–433 (1998); Iqbal, K. et al., *J Neural Transm Suppl* 53:169–180 (1998)). At the same time, since depletion of Pin1 induces mitotic arrest and apoptosis (Lu, K. P. et al., *Nature* 380:544–547 (1996)), sequestration of Pin1 to PHFs itself might also have a deleterious effect on neurons. Therefore, both depletion of Pin1 and formation of PHFs can contribute to neuronal loss in AD. Since the aggregates of hyperphosphorylated tau are also a common neuropathological feature of several other neuronal degenerative diseases, such FTDP-17 (Spillantini, M. G. et al., *Brain Pathol* 8:387–402 (1998); Reed, L. A. et al., *J Neuropathol Exp Neurol* 57:588–601 (1998)) Pin1 can potentially be involved in these diseases. Therefore, Pin1 can be a target for administration utilizing gene therapy. The administration of Pin1, its WW-domain or WW-domain mimic can protect and prevent neurons from undergoing cell death (apoptosis, necrosis) or restore neuronal function in disease states (e.g., Alzheimer's, corticob degeneration, Myotonic dystrophy).

EQUIVALENTS

While this invention has been particularly shown and described with references to preferred embodiments thereof, it will be understood by those skilled in the art that various changes in form and details may be made therein without departing from the spirit and scope of the invention as defined by the appended claims.

What is claimed is:

1. A method of inhibiting the prolyl-peptidyl cis-trans isomerase activity of a Pin1 polypeptide in a cell comprising, contacting a cell expressing Pin-1 with a substance, wherein the substance inhibits the binding of a Pin1 WW-domain with a phosphorylated ligand in the cell.

2. The method of claim 1 wherein the ligand is a mitotic regulatory protein.

3. The method of claim 1 wherein the inhibition comprises competitive inhibition wherein the substance is a phosphorylated ligand mimic that binds to the WW-domain of Pin1, thereby inhibiting the binding of the WW-domain of Pin1 to the ligand.

4. The method of claim 1 wherein the substance is selected from a group consisting of a phosphoserine peptide, a phosphothreonine peptide, a peptide mimetic and a small organic molecule.

5. The method of claim 4 wherein the substance comprises an amino acid sequence selected from the group consisting of: SEQ ID NOS: 8, 10, 13, 20 and 29.

6. The method of claim 1 wherein the inhibition comprises phosphorylating Pin-1 or inhibiting the dephosphorylation of Pin-1, thereby inhibiting the binding of Pin-1 to the ligand.

7. The method of claim 1 wherein the phosphorylated ligand is tau protein.

* * * * *

UNITED STATES PATENT AND TRADEMARK OFFICE
CERTIFICATE OF CORRECTION

PATENT NO.    : 6,495,376 B1
DATED         : December 17, 2002
INVENTOR(S)   : Lu et al.

It is certified that error appears in the above-identified patent and that said Letters Patent is hereby corrected as shown below:

<u>Column 51, lines 42-55 and Column 52, lines 41-52,</u>
Please replace issued claims 1-7 with claims 1-11 as follows:

1. A method of inhibiting the prolyl-peptidyl cis-trans isomerase activity of a Pin1 polypeptide in a cell comprising, contacting a cell expressing Pin-1 with a substance, wherein the substance inhibits the binding of a Pin1 WW-domain with a phosphorylated ligand in the cell.

2. The method of claim 1 wherein the ligand is a mitotic regulatory protein.

3. The method of claim 1 wherein the inhibition comprises competitive inhibition wherein the substance is a phosphorylated ligand mimic that binds to the WW-domain of Pin1, thereby inhibiting the binding of the WW-domain of Pin1 to the ligand.

4. The method of claim 1 wherein the substance is a phosphoserine peptide.

5. The method of claim 4 wherein the substance comprises the amino acid sequence SEQ ID NO: 8.

6. The method of claim 1 wherein the inhibition comprises phosphorylating Pin-1 thereby inhibiting the binding of Pin-1 to the ligand.

7. The method of claim 1 wherein the phosphorylated ligand is tau protein.

8. The method of claim 1 wherein the substance is a phosphothreonine peptide.

9. The method of claim 1 wherein the substance is a peptide mimetic.

10. The method of claim 1 wherein the substance is a small organic molecule.

11. The method of claim 8 wherein the substance comprises the amino acid sequence of SEQ ID NO: 10.

Signed and Sealed this

Seventeenth Day of June, 2003

JAMES E. ROGAN
*Director of the United States Patent and Trademark Office*